US006511966B2

(12) United States Patent
Ghosh et al.

(10) Patent No.: US 6,511,966 B2
(45) Date of Patent: Jan. 28, 2003

(54) MITOCHONDRIA PROTECTING AGENTS FOR TREATING MITOCHONDRIA ASSOCIATED DISEASES

(75) Inventors: Soumitra S. Ghosh, San Diego, CA (US); Scott W. Miller, San Marcos, CA (US); Robert E. Davis, San Diego, CA (US); Walter H. Moos, Oakland, CA (US)

(73) Assignee: MitoKor, San Diego, CA (US)

( * ) Notice: Subject to any disclaimer, the term of this patent is extended or adjusted under 35 U.S.C. 154(b) by 0 days.

(21) Appl. No.: 09/933,911

(22) Filed: Aug. 20, 2001

(65) Prior Publication Data
US 2002/0065298 A1 May 30, 2002

Related U.S. Application Data

(60) Continuation of application No. 09/461,485, filed on Dec. 14, 1999, now abandoned, which is a division of application No. 09/237,999, filed on Jan. 26, 1999, now abandoned.
(60) Provisional application No. 60/072,484, filed on Jan. 26, 1998, provisional application No. 60/072,487, filed on Jan. 26, 1998, provisional application No. 60/072,483, filed on Jan. 26, 1998, and provisional application No. 60/072,482, filed on Jan. 26, 1998.

(51) Int. Cl.$^7$ .............................. A01N 43/04

(52) U.S. Cl. ................... 514/34; 514/312; 546/168

(58) Field of Search ................... 546/168; 514/3 R, 514/311

(56) References Cited

U.S. PATENT DOCUMENTS

| | | | |
|---|---|---|---|
| 3,833,400 A | 9/1974 | Matsukawa et al. ....... 117/36.2 |
| 4,055,567 A | 10/1977 | Murtha ....................... 260/206 |
| 4,087,561 A | 5/1978 | Bharucha et al. ........... 426/266 |
| 4,305,932 A | 12/1981 | Menachemoff et al. ..... 424/180 |
| 4,312,887 A | 1/1982 | Haviv ........................ 424/330 |
| 4,327,224 A | 4/1982 | Archer ....................... 560/142 |
| 4,452,816 A | 6/1984 | Philion ....................... 424/330 |
| 4,511,685 A | 4/1985 | Nissen et al. ............... 524/110 |
| 4,645,845 A | 2/1987 | Gehrken et al. ............ 549/407 |
| 4,661,636 A | 4/1987 | Englert et al. .............. 568/31 |
| 4,695,590 A | 9/1987 | Lippman ..................... 514/724 |
| 4,751,246 A | 6/1988 | Philion ....................... 514/649 |
| 4,877,881 A | 10/1989 | Belliotti et al. ............. 548/240 |
| 4,924,002 A | 5/1990 | Kostlan ...................... 548/206 |
| 5,055,598 A | 10/1991 | Ohuchida et al. ........... 549/407 |
| 5,135,945 A | 8/1992 | Robinson et al. ........... 514/456 |
| 5,208,251 A | 5/1993 | Belliotti et al. ............. 514/372 |
| 5,233,056 A | 8/1993 | Takano et al. .............. 549/407 |
| 5,262,056 A | 11/1993 | Koros et al. ................ 210/654 |
| 5,643,943 A | 7/1997 | Gamache et al. ........... 514/456 |
| 5,847,238 A | 12/1998 | Muralidhara et al. ....... 568/816 |
| 5,925,673 A | 7/1999 | Hellberg et al. ............ 514/465 |

FOREIGN PATENT DOCUMENTS

| | | |
|---|---|---|
| DE | 2156371 | 5/1972 |
| EP | 0 261 977 A2 | 3/1988 |
| EP | 0 382 213 A2 | 8/1990 |
| EP | 0 387 725 A2 | 9/1990 |
| EP | 0 445 735 A1 | 9/1991 |
| EP | 0 460 703 A1 | 12/1991 |
| EP | 0 669 132 A1 | 8/1995 |
| EP | 0 750 911 A1 | 1/1997 |
| FR | 1 584 795 | 1/1970 |
| FR | 2 727 414 A1 | 5/1996 |
| GB | 1 459 420 | 12/1976 |
| GB | 1 544 872 | 4/1979 |
| JP | 63-58455 | 3/1988 |
| WO | WO 94/09162 | 4/1994 |
| WO | WO 95/00494 | 1/1995 |
| WO | WO 96/05191 | 2/1996 |
| WO | WO 96/30012 | 10/1996 |
| WO | WO 97/13504 | 4/1997 |
| WO | WO 98/23567 | 6/1998 |
| WO | WO 98/36748 | 8/1998 |
| WO | WO 98/47534 | 10/1998 |
| WO | WO 99/26954 | 6/1999 |
| WO | WO 99/37294 | 7/1999 |

OTHER PUBLICATIONS

Magura, I.S., Chemical Abstracts 132:11194, abstract of 'Oxicative stress and neurodegenerative disorders', Biopolimery i Kletka, 1997, 13(6), pp513–515.*

Miwa, Ichitomo, Chemical Abstracts 129:26357, abstract of Active oxygen and diabetic complications, Naibunpi, Tonyobyoka, vol. 4(5), pp473–479, 1997.*

Phillis, John W., Chemical Abstracts 129:147375, abstract of "Oxygen free radical involvement in cerebral ischemia/reperfusion injury", 1997, pp. 15–39.*

Cash et al., "Studies on the Antioxidant Action of Thyroxine and Related Compounds," *J. Med. Chem.* 10(6):1081–1085, 1967.

Ebner and Braselton, Jr., "Structural and Chemical Requirements for Hydroxychlorobiphenyls to Uncouple Rat Liver Mitchondria and Potentiation of Uncoupling with Aroclor 1254," *Chem. Biol. Interact.* 63(2):139–155, 1987.

(List continued on next page.)

*Primary Examiner*—D. Margaret Seaman
(74) *Attorney, Agent, or Firm*—Seed IP Law Group PLLC

(57) ABSTRACT

The present invention relates generally to mitochondria protecting agents for treating diseases in which mitochondrial dysfunction leads to tissue degeneration and, more specifically, to compounds, compositions and methods related to the same. The methods of this invention involve administration of a pharmaceutically effective amount of a mitochondria protecting agent to a warm-blooded animal in need thereof, and composition of this invention contain a mitochondria protecting agent in combination with a pharmaceutically acceptable carrier or diluent. Mitochondrial associated diseases which may be treated by the present invention include (but are not limited to) Alzheimer's Disease, diabetes mellitus. Parkinson's Disease, neuronal and cardiac ischemia. Huntington's disease and stroke.

9 Claims, No Drawings

OTHER PUBLICATIONS

Fones et al., "Tert–Butyl–4–Hydroxyanisole as an Inhibitor of Tumor Cell Respiration," STN Database Accession No. 112:48362, 1989.

Horrum et al., "Free Radical Theory of Aging: Effects of Antioxidants on Mitochondrial Function," *Age* 10(2):58–61, 1987.

Isliker et al., "Stabilization of Rat Heart Mitochondria by α–Tocophero in Rats," *Inv. J. Vit. Nutr. Res.* 67(2):91–94, 1997.

Jaarsveld et al., "Antioxidant Supplementation Partially Protects Against Myocardial Mitochondrial Ischemia/Reperfusion Injury, But Ascorbate in the Prefusate Prevented the Beneficial Effect," *Research Communications in Molecular Pathology and Pharmacology* 85(1):33–44, 1994.

Lippman, "Chemiluminescent Measurement of Free Radicals and Antioxidant Molecular–Protection Inside Living Rat Mitochondria," *Exp. Geront.* 15(5):339–351, 1980.

Luft, *Mitochondria & Free Radicals in Neurodegenerative Diseases*, Beal, Howell and Bodis–Wollner, Eds., Wiley–Liss, New York, 1998, Chapter 1, "Historical Overview of Mitochondrial Diseases," pp. 3–14.

Luft, "The Development of Mitochondrial Medicine," *Proc. Natl. Acad. Sci USA* 91(19):8731–8738, 1994.

Meydani et al., "Antioxidants in Experimental Amyloidosis of Young and Old Mice" *Proceedings of the International Symposium of Amyloidosis*, 1986, pp. 683–690.

Nelson, "Cyclooxygenase Inhibitors," in Anthony L. Willis, Ph.D. (ed.), *CRC Handbook of Eicosanoids: Prostaglandins and Related Lipids: Volume II Drugs Acting via the Eicosanoids*, CRC Press, Inc., Boca Raton, Florida, pp. 59–133.

Petit et al., "Mitochondria and Programmed Cell Death: Back to the Future," *FEBS Letters* 396:7–13, 1996.

Plumb et al., "Effect of Ethoxyquin on Glutathione Levels and Peroxidisability of Rat Liver Membranes," *Biochemical Society Transactions* 24(3):380S, 1996.

Uhr et al., "Aromatic Alcohols as Neuroprotectants," *J. Neural Transm.* 54(Suppl.):287–294, 1998.

Verhaeren, "the Uncoupling Activity of Substituted Anthracene Derivatives on Isolated Mitochondria from *Phaseolus Aureus*," *Phytochemistry* 19(4):501–503, 1980.

Walpole et al., "Analogues of Capsaicin with Agonist Activity as Novel Analgesic Agents; Structure–Activity Studies. 2. The Amide Bond 'B–Region,'" *J. Med. Chem.* 36:2373–2380, 1993.

Yu et al., "Benzylamine Antioxidants: Relationship Between Structure, Peroxyl Radical Scavenging, Lipid Peroxidation Inhibition, and Cytoprotection," *J. Med. Chem.* 36:1262–1271, 1993.

Abstract of JP 63–58455, Mar. 14, 1988.
Abstract of JP 10–287559, Oct. 27, 1998.
CA 82:3105, Abstract of Dvinskaya, *Byull, Bses. Nauchno–Issled. Inst* 7(2):50–52, 1973.
CA 85:61810, Abstract of Ivanov, *Byull. Nauchno–Issled. Inst. Fiziol. Biokhim. Pitan. S–kh. Zhivotn.* 9(1):39–41, 1975.
CA 85:76594, Abstract of Dvinskaya, *Fiziol.–Biokhim. Obosnovanie Normirovaniya*, 37–38, 1975.
CA 87:97050, Abstract of Kahl, *Toxicol. Appl. Pharamacol.* 40(3):473–483, 1977.
CA 89:17930, Abstract of Nafstod, *Toxicol. Lett* 1(5–6):295–299, 1978.
CA 99:68992, Abstract of Eisele, *Food Chem. Toxicol.* 21(3):273–277, 1983.
CA 99:28106, Abstract of Srivastava, *Indian J. Pharm. Sci.* 45(1):26–28, 1983.
CA 107:31130 Abstract of JP 61279855, Dec., 1986.
CA 111:79935 Abstract of Graham, *Polym. Mater. Sci. Eng.* 60:31–35, 1989.
CA 112:234967 Abstract of JP 01299262, Dec., 1989.
CA 114:218140 Abstract of JP 02225080, Sep., 1990.
CA 115:135703 Abstract of EP 428385, May, 1991.
CA 115:279581 Abstract of EP 446722, Sep., 1991.
CA 118:23594 Abstract of JP 04220442, Aug., 1992.
CA 119:188611 Abstract of JP 05170687, Jul., 1993.
CA 119:188612 Abstract of JP 05170690, Jul., 1993.
CA 121:133387 Abstract of Nishiyama, *Can. J. Chem.* 72(5):1412–1414, 1994.
CA 121:255396 Abstract of JP 06184004, Jul., 1994.
CA 123:285501 Abstract of EP 648729, Apr. 1995.
CA 123:6187 Abstract of Li, *Neuron* 14(5): 1065–1074, 1995.
CA 125:238222 Abstract of Tatsushi, *Metab. Clin. Exp.* 45(9):1168–1173, 1996.
CA 129:36256 Abstract of Turner, *Dissertation Abstr. Int. B.* 59(1), p. 171, 1997.
CA 129:225084, Abstract of Sudo, *J. Chromatogr.* 813(1):35–45, 1998.
CA 130:7409, Abstract of JP 10287559, Apr. 6, 1998.
World Patent Index, Accession No. 70–40981R\197023. See also FR 1 584 795.
World Patent Index, Accession No. 96–277699/199628. See also FR 2 727 414 A1.

* cited by examiner

MITOCHONDRIA PROTECTING AGENTS FOR TREATING MITOCHONDRIA ASSOCIATED DISEASES

CROSS-REFERENCE TO RELATED APPLICATIONS

This applications of U.S. patent application Ser. No. 09/461,485, filed Dec. 14, 1999 now abandoned; which is a divisional of U.S. patent application Ser. No. 09/237,999, filed Jan. 26, 1999 now abandoned, which claims the benefit of U.S. Provisional Application Nos. 60/072,484, 60/072,487, 60/072,483 and 60/072,482, all filed Jan. 26, 1998.

THE TECHNICAL FIELD

The present invention relates generally to mitochondria protecting agents for treating diseases in which mitochondrial dysfunction leads to tissue degeneration and, more specifically, to compounds, compositions and methods for treating such diseases.

BACKGROUND OF THE INVENTION

Mitochondria are the subcellular organelles that manufacture essential adenosine triphosphate (ATP) by oxidative phosphorylation. A number of degenerative diseases may be caused by or associated with either direct or indirect alterations in mitochondrial function. These include Alzheimer's Disease, diabetes mellitus, Parkinson's Disease, neuronal and cardiac ischemia, Huntington's disease and other related polyglutamine diseases (spinalbulbar muscular atrophy, Machado-Joseph disease (SCA-3), dentatorubropallidoluysian atrophy (DRPLA) and spinocerebellar ataxias 1, 2 and 6), dystonia. Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF).

Defective mitochondrial activity, including but not limited to failure at any step of the elaborate multi-complex mitochondrial assembly, known as the electron transport chain (ETC), may result in 1) decreases in ATP production, 2) increases in the generation of highly reactive free radicals (e.g., superoxide, peroxynitrite and hydroxyl radicals, and hydrogen peroxide). 3) disturbances in intracellular calcium homeostasis and/or 4) release of apoptosis inducing factors such as, e.g., cytochrome c. Because of these biochemical changes, mitochondrial dysfunction has the potential to cause widespread damage to cells and tissues For example, oxygen free radical induced lipid peroxidation is a well established pathogenetic mechanism in central nervous system (CNS) injury such as that found in a number of degenerative diseases, and in ischemia (i.e., stroke).

Mitochondrial dysfunction also is thought to be critical in the cascade of events leading to apoptosis in various cell types (Kroemer et al., FASEB J. 9:1277–87, 1995). Altered mitochondrial physiology may be among the earliest events in apoptosis (Zamzami et al., J. Exp. Med. 182:367–77, 1995; Zamzami et al., J. Exp. Med. 181:1661–72, 1995. In several cell types, including neurons, reduction in the mitochondrial membrane potential ($\Delta\psi$m), a sign of mitochondrial dysfunction, precedes the nuclear DNA degradation that accompanies apoptosis. In cell-free systems, mitochondrial, but not nuclear, enriched fractions are capable of inducing nuclear apoptosis (Newmeyer et al., Cell 70:353–64, 1994). Perturbation of mitochondrial respiratory activity leading to altered cellular metabolic states may occur in mitochondria associated diseases and may further induce pathogenetic events via apoptotic mechanisms. For example, altered mitochondrial activity may lead to undesirable elevated levels of intracellular reactive oxygen species (ROS) and subsequent intracellular damage or cell death.

Stressed (e.g., stressors included free radicals, high intracellular calcium. loss of ATP, among others) mitochondria may release preformed soluble factors that can initiate apoptosis through an interaction with novel apoptosomes (Marchetti et al., Cancer Res. 56:2033–38, 1996; Li et al., Cell 91:479–89, 1997). Release of preformed soluble factors by stressed mitochondria, like cytochrome c, may occur as a consequence of a number events. In some cases, release of apoptotic molecules (apoptoqens) occurs when mitochondria undergo a sudden change in permeability to cytosolic solutes under 1.5 KDa. This process has been termed permeability "transition". In other cases, the permeability may be more subtle and perhaps more localized to restricted regions of a mitochondrion. In still other cases, overt permeability transition may not occur but apoptogens can still be released as a consequence of mitochondrial abnormalities. Thus, changes in mitochondrial physiology may be important mediators of apoptosis. To the extent that apoptotic cell death is a prominent feature of degenerative diseases, mitochondrial dysfunction may be a critical factor in disease progression.

Diabetes mellitus is a common, degenerative disease affecting 5 to 10 percent of the population in developed countries. The propensity for developing diabetes mellitus is reportedly maternally inherited, suggesting a mitochondrial genetic involvement (Alcolado et al., Br. Med. J. 302:1178–1180, 1991; Reny, International J. Epidem. 23:886–890, 1994). Diabetes is a heterogeneous disorder with a strong genetic component; monozygotic twins are highly concordant and there is a high incidence of the disease among first degree relatives of affected individuals.

At the cellular level the degenerative phenotype that may be characteristic of late onset diabetes mellitus includes indicators of altered mitochondrial respiratory function for example impaired insulin secretion and responsivity decreased ATP synthesis and increased levels of reactive oxygen species. Studies have shown that diabetes mellitus may be preceded by or associated with certain related disorders. For example, it is estimated that tort million individuals in the U.S. suffer from late onset impaired glucose tolerance (IGT). IGT patients fail to respond to glucose with increased insulin secretion. A small percentage (5–10%) of IGT individuals progress to insulin deficient non-insulin dependent diabetes (NIDDM) each year. Some of these individuals further progress to insulin dependent diabetes mellitus (IDDM). These forms of diabetes mellitus. NIDDM and IDDM, are associated with decreased release of insulin by pancreatic beta cells and/or a decreased end-organ response to insulin. Other symptoms of diabetes mellitus and conditions that precede or are associated with diabetes mellitus include obesity, vascular pathologies, peripheral and sensory neuropathies, blindness and deafness.

Due to the strong genetic component of diabetes mellitus, the nuclear genome has been the main focus of the search for causative genetic mutations. However, despite intense effort, nuclear genes that segregate with diabetes mellitus are known only for rare mutations in the insulin gene, the insulin receptor gene, the adenosine deaminase gene and the glucokinase gene. Accordingly, mitochondrial defects, which may include but need not be limited to defects related to the discrete non-nuclear mitochondrial genome that resides in mitochondrial DNA, may contribute significantly to the pathogenesis of diabetes mellitus.

Parkinson's disease (PD) is a progressive, mitochondria associated neurodegenerative disorder characterized by the loss and/or atrophy of dopamine-containing neurons in the pars compacta of the substantia nigra of the brain. Like Alzheimer's Disease (AD), PD also afflicts the elderly. It is characterized by bradykinesia (slow movement), rigidity and a resting tremor. Although L-Dopa treatment reduces tremors in most patients for a while, ultimately the tremors become more and more uncontrollable, making it difficult or impossible for patients to even feed themselves or meet their own basic hygiene needs.

It has been shown that the neurotoxin 1-methyl-4-phenyl-1,2,3,6-tetrahydropyridine (MPTP) induces parkinsonism in animals and man, at least in part through its effects on mitochondria. MPTP is converted to its active metabolite, $MPP^-$, in dopamine neurons; it then becomes concentrated in the mitochondria. The MPP then selectively inhibits the mitochondrial enzyme NADH:ubiquinone oxidoreductase ("Complex I"), leading to the increased production of free radicals, reduced production of adenosine triphosphate and. ultimately the death of affected dopamine neurons.

Mitochondrial Complex I is composed of 40–50 subunits, most are encoded by the nuclear genome and seven by the mitochondrial genome. Since parkinsonism may be induced by exposure to mitochondrial toxins that affect Complex I activity, it appears likely that defects in Complex I proteins may contribute to the pathogenesis of PD by causing a similar biochemical deficiency in Complex I activity. Indeed, defects in mitochondrial Complex I activity have been reported in the blood and brain of PD patients (Parker et al., *Am. J. Neurol.* 26:719–723, 1989).

Similar theories have been advanced for analogous relationships between mitochondrial defects and other neurological diseases, including Alzheimer's disease (AD), Leber's hereditary optic neuropathy, schizophrenia, "mitochondrial encephalopathy, lactic acidosis and stroke" (MELAS), and "myoclonic epilepsy ragged red fiber syndrome" (MERRF).

For example, AD is a progressive neurodegenerative disorder that is characterized by loss and/or atrophy of neurons in discrete regions of the brain, and that is accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they cease to recognize family and loved ones, and they often require continuous care until their eventual death.

There is evidence that defects in oxidative phosphorylation within the mitochondria are at least a partial cause of sporadic AD. The enzyme cytochrome c oxidase (COX), which makes up part of the mitochondrial electron transport chain (ETC), is present in normal amounts in AD patients; however, the catalytic activity of this enzyme in AD patients and in the brains of AD patients at autopsy has been found to be abnormally low (Parker et al., *Neurology* 44:1086–1090, 1994). This suggests that the COX in AD patients is defective, leading to decreased catalytic activity that in some fashion causes or contributes to the symptoms that are characteristic of AD.

One hallmark pathology of AD is the death of selected neuronal populations in discrete regions of the brain. Cell death in AD is presumed to be apoptotic because signs of cell death are observed whereas indicators of active gliosis and necrosis are not (Smale et al., *Exp. Neiurolog.* 133:225–230, 1995; Cotman et al., *Molec. Neurobiol.* 10:19–45, 1995). The consequences of cell death in AD, neuronal and synaptic loss, are closely associated with the clinical diagnosis of AD and are highly correlated with the degree of dementia in AD (DeKosky et al., *Ann. Neurology* 27:457–464, 1990).

Indeed. focal defects in energy metabolism in the mitochondria, with accompanying increases in oxidative stress, may be associated with AD. It is well-established that energy metabolism is impaired in AD brain (Palmer et al., *Brain Res.* 645:338–42, 1994: Pappolla et al., *Am. J. Pathol.* 140:621–28, 1992; Jeandel et al., *Gerontol.* 35:275, 1989: Balazs et al., *Neurochem. Res.* 19:1131–37, 1994; Mecocci et al., *Ann Neurol*, 36:747–751, 1994; Gsell et al., *J. Neurochem.* 64:1216–23, 1995). For example, regionally specific deficits in energy metabolism in AD brains have been reported in a number of positron emission tomography studies (Kuhl, et al., *J. Cereb. Blood Flow Metab.* 7:S406, 1987; Grady, et al., *J. Clin. Exp. Neuropsychol.* 10:576–96, 1988; Haxby et al., *Arch Neurol.* 47:753–60, 1990; Azari et al., *J. Cereb. Blood Flow Metab.* 13:438–47, 1993). Metabolic defects in the temporoparietal neocortex of AD patients apparently presage cognitive decline by several years. Skin fibroblasts from AD patients display decreased glucose utilization and increased oxidation of glucose, leading to the formation of glycosylation end products (Yan et al., *Proc. Nat. Acad. Sci. USA* 91:7787–91, 1994). Cortical tissue from postmortem AD brain shows decreased activity of the mitochondrial enzymes pyruvate dehydrogenase (Sheu et al., *Ann. Neurol* 17:444–49, 1985) and α-ketoglutarate dehydrogenase (Mastrogiacomo et al., *J. Neurochem.* 6:2007–14, 1994), which are both key enzymes in energy metabolism. Functional magnetic resonance spectroscopy studies have shown increased levels of inorganic phosphate relative to phosphocreatine in AD brain, suggesting an accumulation of precursors that arises from decreased ATP production by mitochondria (Pettegrew et al., *Neurobiol Of Aging* 15:117–32, 1994; Pettigrew et al., *Neurobiol. Of Aging* 16:973–75, 1995).

Signs of oxidative injury also are prominent features of AD pathology, and reactive oxygen species (ROS) are critical mediators of neuronal degeneration. Indeed, studies at autopsy show that markers of protein, DNA and lipid peroxidation are increased in AD brain probably as a result of increased ROS production secondary to mitochondrial dysfunction (Palmer et al., *Brain Res.* 645:338–42, 1994; Pappola et al., *Am. J. Pathol.* 140:621–28, 1992; Jeandel et al., *Gerontol.* 35:275–82, 1989; Balazs et al., *Arch. Neurol.* 4:864, 1994; Mecocci et al., *Ann. Neurol.* 36:747–51, 1994; Smith et al., *Proc. Nat. Acad Sci. USA* 88:10540–43, 1991). In hippocampal tissue from AD but not from controls, carbonyl formation indicative of protein oxidation is increased in neuronal cytoplasm, and nuclei of neurons and glia (Smith et al., *Nature* 382:120–21, 1996). Neurofibrillary tangles also appear to be prominent sites of protein oxidation (Schweers et al., *Proc. Nat. Acad. Sci. USA* 92:8463, 1995: Blass et al., *Arch. Neurol.* 4:864, 1990). Under stressed and non-stressed conditions incubation of cortical tissue from AD brains taken at autopsy demonstrate increased free radical production relative to non-AD controls. In addition, the activities increased of critical antioxidant enzymes, particularly catalase, are reduced in AD (Gsell et al., *J. Neurochem.* 64:121623, 1995), suggesting that the AD brain is vulnerable to increased ROS production. Thus, oxidative stress may contribute significantly to the pathology of mitochondria associated diseases such as AD, where mitochondrial dysfunction and/or elevated ROS may be present.

Accordingly, there is a need for compounds, compositions and methods that limit or prevent damage to organelles, cells and tissues initiated by various consequences of mitochondrial dysfunction. In particular, because mitochondria are essential organelles for producing metabolic energy, agents that inhibit the production of, and/or protect mitochondria and cells against, ROS and other sources of injury would be especially useful. Such agents would be suitable for the treatment of degenerative diseases, including mitochondria associated diseases. The present invention fulfills these needs and provides other related advantages.

SUMMARY OF THE INVENTION

Briefly stated, the present invention is directed to the treatment of mitochondria associated diseases by administration to a warm-blooded animal in need thereof an effective amount of a mitochondria protecting agent having one of the following general structures (I) through (IV):

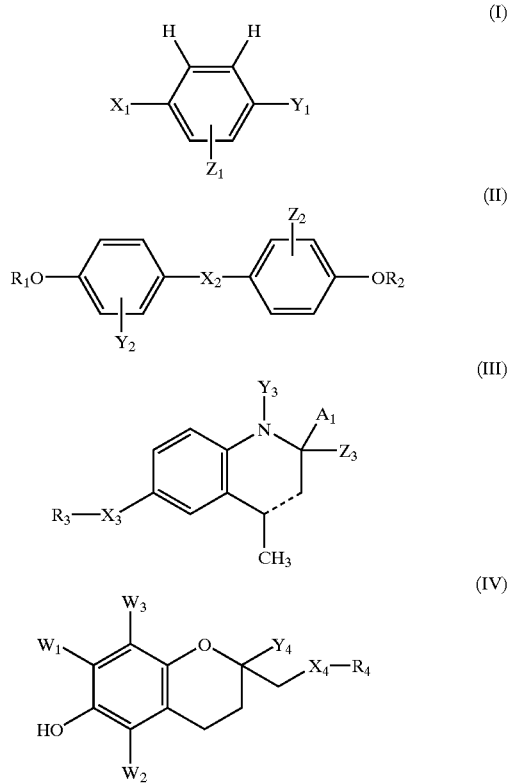

wherein $X_1$, $X_2$, $X_3$, $X_4$, $Y_1$, $Y_2$, $Y_3$, $Y_4$, $Z_1$, $Z_2$, $Z_3$, $W_1$, $W_2$, $W_3$, $A_1$, $R_1$, $R_2$, $R_3$ and $R_4$ are as identified in the following detailed description.

The compounds of this invention have activity over a wide range of mitochondria associated diseases, including (but not limited to) Alzheimer's Disease, diabetes mellitus, Parkinson's Disease, neuronal and cardiac ischemia, Huntington's disease and other related polyglutamine diseases (spinalbulbar muscular atrophy, Machado-Joseph disease (SCA-3), dentatorubro-pallidoluysian atrophy (DRPLA) and spinocerebellar ataxias 1, 2 and 6), dystonia Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF).

Accordingly, this invention is also directed to method of treating a mitochondria associated disease by administration of an pharmaceutically effective mount of a mitochondria protecting agent to a warm-blooded animal in need thereof as well as to pharmaceutical compositions containing a mitochondria protecting agent of this invention in combination with a pharmaceutically acceptable carrier or diluent.

These and other aspects of the present invention will become evident upon reference to the following detailed description and attached drawings. To that end, various references are set forth herein which describe in more detail certain aspects of this invention, and are each incorporated by reference in their entirety.

DETAILED DESCRIPTION OF THE INVENTION

The present invention is generally directed to compounds (also referred herein as "mitochondria protecting agents") and to pharmaceutical compositions containing the same, as well as to methods useful for treating mitochondria associated diseases. More specifically, the mitochondria protecting agents of this invention have an $IC_{50} \leq 50$ μm, typically $\leq 1$ μm preferably $\leq 200$ nM, and more preferably $\leq 70$ nM in the dichlorofluorescin diacetate (DCFC) assay described herein, and have one of the following structures (I) through (IV):

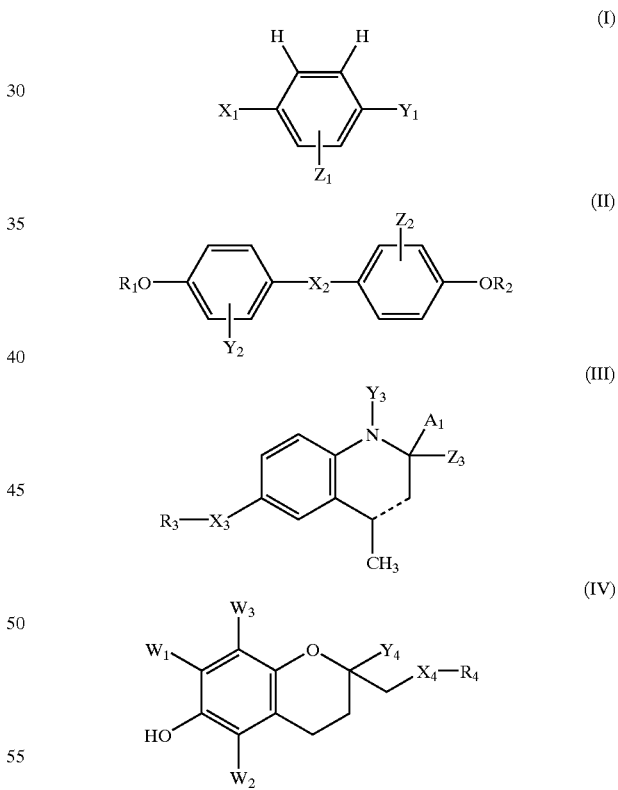

including steroisomers and pharmaceutically acceptable salts thereof,
where in structure (I):
  $X_1$ is selected from —OH, —$OR_a$ and —$OCOCH_3$;
  $Y_1$ is selected from —OH, —$R_aOH$, —$OCOCH_3$ and $C_{1-12}$alkyl;
  $Z_1$ is selected from —H, —$NHH_2$, —OH, —$NO_2$, —$OCOCH_3$ and $C_{1-12}$alkyl; and
  each occurrence of $R_a$ is selected from $C_{1-6}$alkyl;

where in structure (II):

R$_1$ and R$_2$ are independently selected from —H, —C(=O)C$_{1-3}$alkyl and C$_{1-3}$alkyl;

X$_2$ is optionally present and selected from —(A$_2$)(A$_3$)—, —(CH$_2$)$_n$—, —O— and —NH—;

Y$_2$ and Z$_2$ are independently selected from —H, —OH, —NH$_2$, —NO$_2$, —OR$_b$, —NHCNHNH$_2$, —NHR$_b$ and —NR$_b$R$_c$;

A$_2$ and A$_3$ are independently selected from —H and C$_{1-3}$alkyl;

R$_b$ and R$_c$ are independently C$_{1-4}$alkyl; and n is 2–9;

where in structure (III):

the dotted line represents a single or double bond;

A$_1$ is selected from —H and C$_{1-3}$alkyl;

Y$_3$ is selected from —H, C$_{1-3}$alkyl and —COR$_d$;

Z$_3$ is selected from —H, C$_{1-3}$alkyl and —(CH$_)_m$X$_3$R$_d$;

X$_3$ is selected at each occurrence from —S—, —O— and —NH—;

R$_3$ is selected from —H, —CH$_3$, —CH$_2$CH$_3$ and —R$_d$;

R$_d$ is selected from a guanidino moiety, a cylcoguanidino moiety, and a non-steroidal anti-inflammatory drug; and m is 1–4; and where in structure (IV):

W$_1$, W$_2$ and W$_3$ are independently selected from —H and C$_{1-3}$alkyl;

X$_4$ is optionally selected from —NH—, —O— and —S—;

Y$_4$ is selected from —H and C$_{1-12}$alkyl; and

R$_4$ is selected from —H, a guanidino moiety, a cylcoguanidino moiety, and a non-steroidal anti-inflammatory drug, or X$_4$—R$_4$ taken together is selected from —CH$_2$OH, —OC(=O)CH$_3$, and C$_{1-3}$ alkyl.

As used herein, the following terms have the meanings set forth below:

A "C$_{1-12}$ alkyl" is a straight chain or branched, saturated or unsaturated hydrocarbon moiety having from 1 to 12 carbon atoms, such as methyl, ethyl, propyl, isopropyl butyl, isobutyl, tert-butyl and the like, pentyl, the pentyl isomers, hexyl and the hexyl isomers and the higher homologues having up to 12 carbon atoms such as, for example, heptyl, octyl, nonyl, decyl, undecyl, dodecyl and the like. In instances where a hydrocarbon having a different number of carbon atoms is recited, such as "C$_{1-3}$ alkyl", "C$_{1-4}$ alkyl", "C$_{1-6}$ alkyl", "C$_{1-8}$ alkyl" and the like, a straight chain or branched, saturated or unsaturated hydrocarbon moiety is intended, but having the number of carbon atoms indicated.

A "guanidino moiety" and a "cycloguanidino moiety" have the following structure (a) and structure (b), respectively:

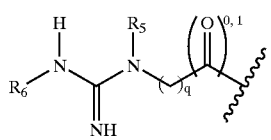

(a)

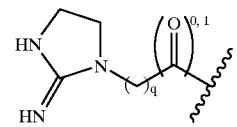

(b)

wherein R$_5$ and R6 are independently selected from —H and C,alkyl, and q is 0–3.

A "non-steroidal antiinflammatory drug" (NSAID) is a NSAID having a carboxylic moiety. A number of chemical classes of NSAID have been identified. The following text, the entire contents of which are hereby incorporated by reference in the present specification, may be referred to for various NSAID chemical classes: CRC Handbook of Eicosanoids: Prostaglandins, and Related Lipids, Volume II, Drugs Acting Via the Eicosanoids, pages 59–133, CRC Press, Boca Raton, Fla. (1989). The NSAID may be selected, therefore, from a variety of chemical classes including, but not limited to, salicylic acid or its derivatives including acetylsalicylic acid, fenamic acids, such as flufenamic acid, nitlumic acid and mefenamic acid; indoles, such as indomethacin, sulindac and tolmetin; phenylalkanoic acids, such as suprofen, ketorolac, flurbiprofen and ibuprofen; and phenylacetic acids, such as dictofenac. Further examples of NSAID include loxoprofen, pirprofen, naproxen, benoxaprofen, aceloferac, fleclozic acid, bromfenac, alcofenac, diflunisal, tolfenamic acid. clidanac, fenclorac, carprofen, fenbufen, amfenac, ketoprofen, orpanoxin, pranoprofen, indoprofen, fenoprofen, meclofenamate, isofezolac, etodolic acid, efenamic acid, fenclofenac, zomopirac, zaltoprofen and other NSAID compounds. The preferred compounds are those wherein the NSAID is selected from the ester or amide derivatives of salicylic acid or its derivatives including acetylsalicylic acid, naproxen, ibuprofen or acetylsalicic acid.

In one aspect, the mitochondria protecting agents of this invention have the following structure (I):

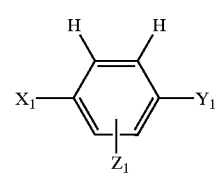

(I)

including steroisomers and pharmaceutically acceptable salts thereof, wherein

X$_1$ is selected from —OH, —OR$_a$ and —OCOCH$_3$;

Y$_1$ is selected from —OH, —R$_a$OH, —OCOCH$_3$ and C$_{1-12}$alkyl;

Z$_1$ is selected from —H, —NH$_2$, —OH, —NO$_2$, —OCOCH$_3$ and C$_{1-12}$alkyl; and each occurrence of R$_a$ is selected from C$_{1-6}$alkyl.

For purpose of clarity, position of Z$_1$ will be referenced by the following numbering:

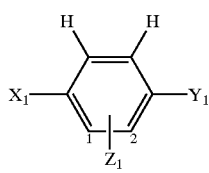

In one embodiment of structure (I), $X_1$ is —OH, $Z_1$ is —NH$_2$, and the compounds of this invention have the following structure (I-1):

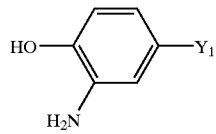

(I-1)

Thus, location of the $Z_1$ substituent in structure (I-1) is referred to herein as a "1—NH$_2$".

In one embodiment of structure (I-1), $Y_1$ is $C_{1-12}$alkyl, such as the following structures (I-2) or (I-3):

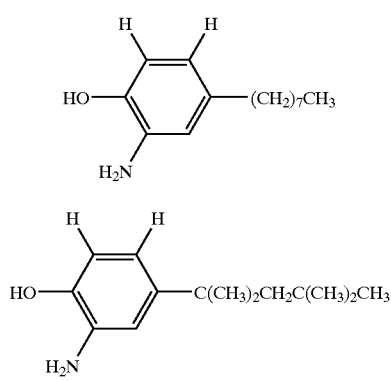

(I-2)

(I-3)

In another embodiment of structure (I), $X_1$ and $Z_1$ are —OH, and the compounds of this invention have the following structure (I-4):

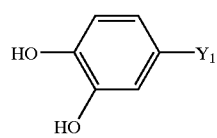

(I-4)

In one embodiment of structure (I-4), $Y_1$ is $C_{1-12}$alkyl, such as the following structures (I-5) or (I-6);

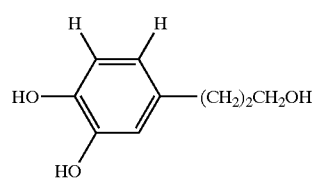

(I-5)

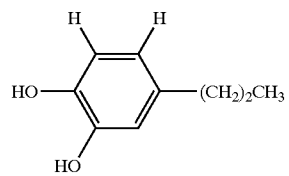

(I-6)

In still another embodiment of structure (I), $X_1$ and $Z_1$ are —OCOCH$_3$, and the compounds of this invention have the following structure (I-7):

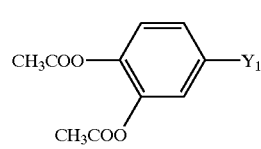

(I-7)

In one embodiment of structure (I-7), $Y_1$ is $C_{1-12}$alkyl, such as the following structure (I-8):

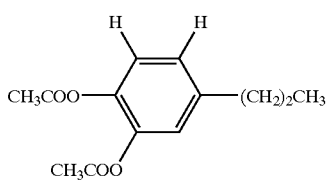

(I-8)

In yet another embodiment of structure (I), $X_1$ and $Y_1$ are —OH, and the compounds of this invention have the following structure (I-9):

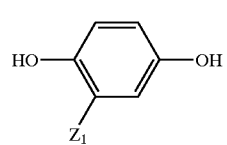

(I-9)

In one embodiment of structure (I-9), $Z_1$ is $C_{1-12}$alkyl, such as the following structure (I-10):

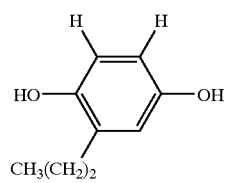

(I-10)

Representative compounds of structure (I) are set forth in the following Table 1.

TABLE 1

Representative Compounds of Structure (I)

| Compound | $X_1$ | $Z_1$ | $Y_1$ | MW |
|---|---|---|---|---|
| (I-2) | OH | 1-$NH_2$ | n-octyl | 221 |
| (I-3) | OH | 1-$NH_2$ | tert-octyl* | 221 |
| (I-5) | OH | 1-OH | $(CH_2)_2CH_2OH$ | 168 |
| (I-6) | OH | 1-OH | n-propyl | 152 |
| (I-8) | $OCOCH_3$ | 1-$OCOCH_3$ | n-propyl | 236 |
| (I-10) | OH | 1-n-propyl | OH | 152 |
| (I-11) | $OCOCH_3$ | 1-n-propyl | $OCOCH_3$ | 236 |
| (I-12) | OH | 2-OH | 2-propenyl | 150 |
| (I-13) | OH | 2-propenyl | OH | 150 |
| (I-14) | $OCH_3$ | 1-$NH_2$ | n-octyl | 235 |
| (I-15) | $OCH_3$ | 1-$NO_2$ | n-octyl | 265 |
| (I-16) | OH | 1-$NO_2$ | n-octyl | 251 |
| (I-17) | OH | 1-$NO_2$ | tert-octyl | 235 |
| (I-18) | $OCOCH_3$ | 1-$NO_2$ | n-octyl | 293 |

| Compound | $^1$H NMR δ (500 MHz, $CDCl_3$) |
|---|---|
| (I-2) | 6.64 (d, 2H), 6.48 (dd, 1H), 2.45 (t, 2H), 1.53 (t, 2H), 1.27 (m, 10H), 0.87 (t, 3H) |
| (I-3) | 6.76 (s, 1H), 6.66 (m, 2H), 1.66 (s, 2H), 1.30 (s, 6H), 0.73 (s, 9H) |
| (I-5) | 6.64 (m, 2H), 6.51 (m, 1H), 3.54 (t, 2H), 2.51 (t, 2H), 1.76 (m, 2H) (in $CD_3OD$) |
| (I-6) | 6.75 (d, 1H), 6.69 (d, 1H), 6.61 (dd, 1H), 2.47 (t, 2H), 1.57 (m, 2H), 0.91 (t, 3H) |
| (I-8) | 7.05 (m, 2H), 7.0 (d, 1H), 2.57 (t, 2H), 2.28 (s, 3H), 2.27 (s, 3H), 1.62 (m, 2H), 0.94 (T, 3H) |
| (I-10) | 6.71 (m, 3H), 5.15 (s, 1H), 5.12 (s, 1H), 2.59 (t, 2H), 1.64 (m, 2H), 0.97(t, 3H) |
| (I-11) | 7.20–7.03 (m, 3H), 2.50 (t, 2H), 2.32 (s, 3H), 2.27 (s, 3H), 1.61 (m, 2H), 0.95 (t, 3H) |
| (I-14) | 7.66 (m, 1H), 7.35–7.33 (m, 1H), 6.99 (d, 1H), 3.93 (s, 3H), 2.59 (t, 2H), 1.61–1.56 (m, 2H), 1.30–1.26 (m, 10H), 0.88 (t, 3H) |
| (I-15) | 6.70 (d, 1H), 6.56–6.52 (m, 2H), 3.82 (s, 3H), 2.46 (t, 2H), 1.58–1.52 (m, 2H), 1.29–1.26 (m, 10H), 0.87 (t, 3H) |
| (I-16) | 10.46 (s, 1H), 7.89 (d, 1H), 7.40 (dd, 1H), 7.07 (d, 1H), 2.59 (t, 2H), 1.60 (m, 2H), 1.32–1.23 (m, 10H), 0.88 (t, 3H) |

*tert-octyl = $C(CH_3)_2CH_2C(CH_3)_2CH_3$

The compounds of structure (I) may be made by know organic reaction techniques, including those set forth in Example 6 below. For example. as depicted below under reaction "a", representative alkyl analogues at position $Y_1$ may be synthesized from the corresponding allyl as the starting material (such as eugenol for n-propyl) and involve hydrogenation of the allyl bond, followed by deprotection of the methyl ether using boron tribromide. Alternatively, as depicted by reaction "b", the corresponding alkyl-phenol analogue may be employed as the starting material. followed by addition of the desired $Z_1$ substituent. For example, alkyl phenol derivatives may be made by nitration using nitric acid, optionally followed by reduction with activated iron. In yet a further variation, the alkyl $Z_1$ substituents can be introduced via Friedel Crafts alkylation of alkyl phenols via reaction "b". Similarly, hydroxyalkylation of alkyl phenols can be achieved via treatment with an aldehyde and boron containing reagents, such as benzeneboronic acid.

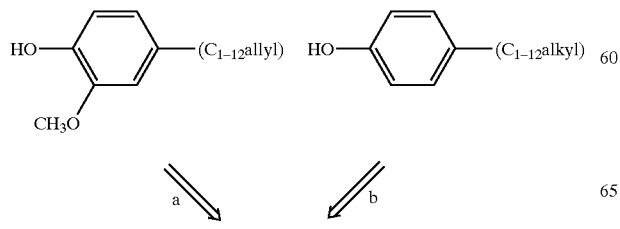

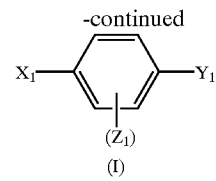

In addition, it should be recognized that the starting materials for the synthesis of compounds of structure (I) are commercially available from a number of sources.

In another aspect, the mitochondria protecting agents of this invention have the following structure (II):

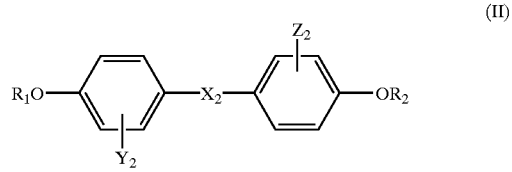

including steroisomers and pharmaceutically acceptable salts thereof, wherein $R_1$ and $R_2$ are independently selected from —H, —C(=O)$C_{1-3}$alkyl and $C_{1-3}$alkyl;

$X_2$ is optionally present and selected from —C($A_2$)($A_3$)—, —$(CH_2)_n$—, —O— and —NH—;

$Y_2$ and $Z_2$ are independently selected from —H, —OH, —$NH_2$, —$NO_2$, —$OR_b$, —NHCNHN$H_2$, —$NHR_b$ and —$NR_bR_c$;

$A_2$ and $A_3$ are independently selected from —H and $C_{1-3}$alkyl;

$R_b$ and $R_c$ are independently $C_{1-4}$alkyl and n is 2–9.

For purpose of clarity, position of $Y_2$ and $Z_1$ will be referenced by the following numbering:

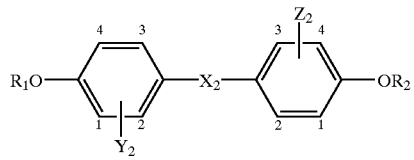

In one embodiment of structure (II), $R_1$ and $R_2$ are —H, $Y_2$ and $Z_2$ are —$NH_2$, and the compounds of this invention has the following structure (II-1):

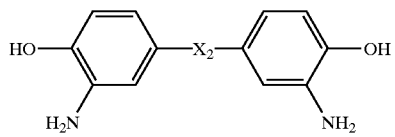
(II-1)

In one embodiment of structure (II1), $X^2$ is —C($A_2$)($A_3$)—, such as the following structure (II-2):

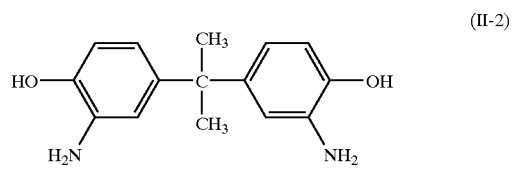
(II-2)

In another embodiment of structure (II), $R_1$ and $R_2$ are —H, $Y_2$ is —H and $Z_2$ is —$NH_2$, and the compounds of this invention has the following structure (II-3):

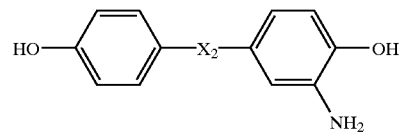

Representative compounds of structure (II) are set forth in the following Table 2.

TABLE 2

Representative Compounds of Structure (II)

| Cpd. | $R_1$ | $R_2$ | $X_2$ | $Y_2$ | $Z_2$ | MW |
|---|---|---|---|---|---|---|
| (II-2) | H | H | —C(CH$_3$)$_2$— | 1-NH$_2$ | 1-NH$_2$ | 258 |
| (II-4) | H | H | —C(CH$_3$)$_2$— | H | 1-NH$_2$ | 243 |
| (II-5) | H | H | —C(CH$_3$)$_2$— | H | H | 228 |
| (II-6) | H | H | —C(CH$_3$)$_2$— | 1-N(CH$_3$)$_2$ | 1-N(CH$_3$)$_2$ | 314 |
| (II-7) | H | H | —C(CH$_3$)$_2$— | 1-NO$_2$ | 1-NO$_2$ | 318 |
| (II-8) | H | H | —C(CH$_3$)$_2$— | H | 1-NO$_2$ | 273 |
| (II-9) | CH$_3$ | CH$_3$ | —C(CH$_3$)$_2$— | H | 1-NH$_2$ | 271 |
| (II-10) | H | H | —C(CH$_3$)$_2$— | H | 1-NHC(=NH)NH$_2$ | 285 |
| (II-11) | H | H | —C(CH$_3$)$_2$— | H | 1-N(CH$_3$)$_2$ | 271 |
| (II-12) | COCH$_3$ | COCH$_3$ | —C(CH$_3$)$_2$— | H | 1-NO$_2$ | 333 |

| Compound | $^1$H NMR δ (500 MHz, CDCl$_3$) |
|---|---|
| (II-2) | 6.61 (d, 2H), 6.56 (d, 2H), 6.49 (dd, 2H), 1.52 (s, 6H). |
| (II-4) | 7.02 (dd, 2H), 6.58–6.65 (M, 4H), 6.50 (DD, 1H), 1.55 (S, 6H) |
| (II-6) | 6.84–6.80 (m, 6H), 6.68 (d, 2H), 2.61 (s, 12H), 1.58 (s, 6H) (in CD$_3$OD) |
| (II-7) | 10.54 (s, 2H), 8.04 (d, 2H), 7.33 (dd, 2H), 7.08 (d, 2H), 1.70 (s, 6H) |
| (II-8) | 10.52 (s, 1H), 8.05 (d, 1H), 7.34 (dd, 1H), 7.07–7.02 (m, 3H), 6.76–6.74 (m, 2H), 4.73 (s, 1H), 1.65 (s, 6H) |
| (II-9) | 6.69–6.56 (m, 7H), 3.73 (s, 6H), 1.58 (s, 6H) |
| (II-10) | 7.10–6.67 (m, 7H), 1.60 (s, 6H) |
| (II-11) | 7.09–6.72 (m, 7H), 2.60 (s, 6H), 1.62 (s, 6H) |

The compounds of structure (II) may be made by know organic reaction techniques, including those set forth in Example 7 below. For example, representative compounds of structure (II) may be made from the corresponding diphenol (such by 4,4-isopropylidenediphenol) as starting material as represented below by reaction "a". Nitration provides the mono- and di-nitro derivatives that can be separated by silica gel chromatography. Reduction of the nitro groups provide the corresponding amines. The amines can be further modified by reductive amination using paraformaldehyde and sodium cyanoborohydride. 4,4-isopropyldenediphenol can be reacted with methyl iodide in the presence of potassium carbonate to provide, for example, the monomethyl and dimethyl ethers via reaction "b", which ethers may be separated by silica gel chromatography. These dialkyloxy derivatives may require more severe nitrating conditions, and nitronium tetrafluoroborate may be utilized to furnish the mono- and di-nitro systems as depicted by reaction "c". Reduction of the nitro functionalities may be achieved using iron in aqueous acetic acid.

each occurrence of $X_3$ is selected from —S—, —O— and —NH—;

$R_3$ is selected from —H, —CH$_3$, —CH$_2$CH$_3$ and —R$_d$;

$R_d$ is selected from a guanidino moiety, a cylcoguanidino moiety, and a non-steroidal anti-inflammatory drug; and m is 1–4.

In one embodiment of structure (III), $R_3$ is $R_d$, and $R_d$ is a guanidino moiety, and the compounds of this invention have the following structure (III-1):

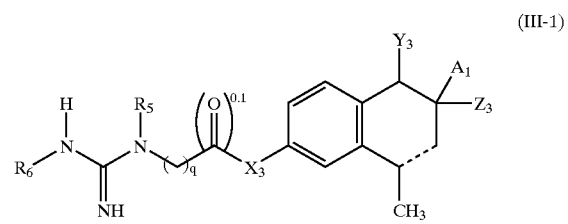

(III-1)

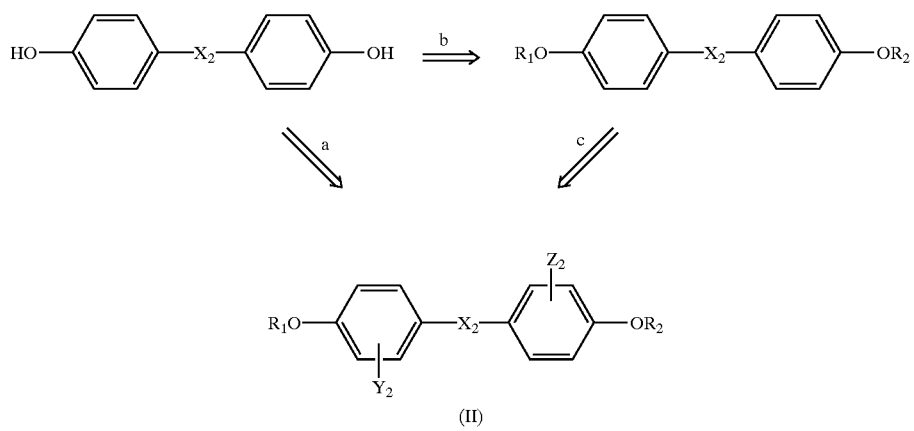

In addition, it should be recognized that some of the compounds of structure (II), including starting materials therefor, are commercially available from a number of sources. Further, various references disclose additional techniques, such as published Japanese Application Nos. JP 07/278038 A2 to Hozumi et al. and JP 05/125180 A2 to Endo et al. (both of which are incorporated herein by reference), for the synthesis of compounds of structure (II).

In another aspect, the mitochondria protecting agents of this invention have the following structure (III):

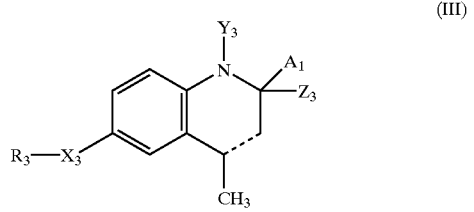

(III)

including steroisomers and pharmaceutically acceptable salts thereof, wherein the dotted line represents a single or double bond;

$A_1$ is selected from —H and $C_{1-3}$alkyl;

$Y_3$ is selected from —H, $C_{1-3}$alkyl and —COR$_d$;

$Z_3$ is selected from —H, $C_{1-3}$alkyl and —(CH$_2$)$_m$X$_3$R$_d$;

In another embodiment of structure (III), $R_3$ is $R_d$, $R_d$ is a cycloguanidino moiety, and the compounds of this invention have the following structure (III-2):

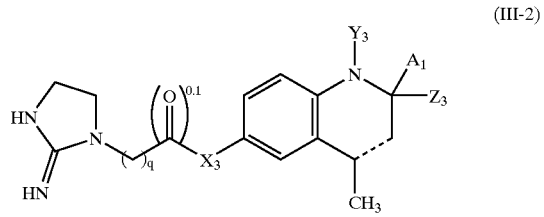

(III-2)

In still a further embodiment of structure (III), $Y_3$ is —COR$_d$, where $R_d$ is a non-steroidal anti-inflammatory drug (NSAID). Such NSAIDs may be coupled to the nitrogen at the $Y_3$ position by formation of an amide linkage by, for example, reaction between a carboxylic acid moiety (—COOH) of the NSAID and secondary amine of structure (III) (—NH—). Thus, the designation "—COR$_d$" should be understood to represent the formation of such an amide linkage. Representative compounds of this embodiment include those of the following structures (III7), (III-8) and (III-9):

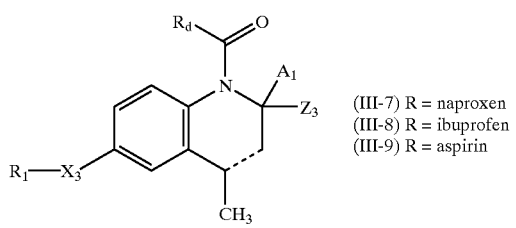

(III-7) R = naproxen
(III-8) R = ibuprofen
(III-9) R = aspirin

Representative compounds of structure (III) are set forth in the following Table 3.

TABLE 3

Representative Compounds of Structure (III)

| Cpd | Bond | $R_3$ | $X_3$ | $A_1$ | $Y_3$ | | $Z_3$ | MW |
|---|---|---|---|---|---|---|---|---|
| (III-3) | double | H | O | $CH_3$ | H | | $CH_3$ | 189 |
| (III-4) | double | $C_2H_5$ | O | $CH_3$ | H | | $CH_3$ | 217 |
| (III-5) | single | $C_2H_5$ | O | $CH_3$ | H | | $CH_3$ | 219 |
| (III-6) | double | $CH_3$ | O | $CH_3$ | H | | $CH_3$ | 203 |
| (III-7) | double | $C_2H_5$ | O | $CH_3$ | —C=O-naproxen | | $CH_3$ | 429 |
| (III-8) | double | $C_2H_5$ | O | $CH_3$ | —C=O-ibuprofen | | $CH_3$ | 405 |
| (III-9) | double | $C_2H_5$ | O | $CH_3$ | —C=O-aspirin | | $CH_3$ | 380 |
| (III-10) | double | H | O | $CH_3$ | $CH_3$ | | $CH_3$ | 203 |

| Compound | $^1$H NMR δ (500 MHz, $CDCl_3$) |
|---|---|
| (III-7) | 7.64–6.68 (m, 9H), 5.39 (s, 1H), 4.12 (q, 1H), 4.06 (q, 2H), 3.90 (s, 3H), 1.88 (s, 3H), 1.58 (s, 3H), 1.55 (d, 3H), 1.45 (t, 3H), 1.31 (s, 3H) |
| (III-8) | 7.09 (br, 2H), 7.01 (d, 2H), 6.76 (s, 1H), 6.67 (s, 2H), 5.41 (s, 1H), 4.05 (m, 3H), 2.41 (d, 2H), 1.95 (s, 3H), 1.82 (m, 1H), 1.57 (s, 3H), 1.47 (d, 3H), 1.44 (t, 3H), 1.30 (s, 3H), 0.88 (d, 6H) |
| (III-9) | 7.44 (d, 1H), 7.30 (m, 1H), 7.11 (t, tH), 6.92 (d, tH), 6.71 (d, 1H), 6.51 (d, 1H), 6.30 (m, 1H), 5.59 (s, 1H), 3.91 (q, 2H), 2.23 (s, 3H), 2.05 (s, 3H), 1.60 (s, 6H), 1.35 (t, 3H) |
| (III-10) | 6.64–6.46 (m, 3H), 5.40 (s, 1H), 2.71 (s, 3H), 1.94 (s, 3H), 1.21 (s, 6H) (in $CD_3OD$) |

The compounds of structure (III) may be made by know organic reaction techniques, including those set forth in Example 8 below. For example, representative compounds of structure (III) may be made from ethoxyquin or suitable 6-substituted 2,2,4-trimethyl, 1,2-dihydroquinolines as depicted below by reaction "a". Alkylation of the secondary amine may be carried out using reductive amination conditions. For example, acylation of the secondary amine to provide the NSAID derivatives may be accomplished by coupling with the corresponding acid halides at elevated temperatures. Alternatively, compounds of structure (III) may be made from the corresponding alcohol (or thiol) by reaction "b", followed by conversion of the alcohol to the desired substituent.

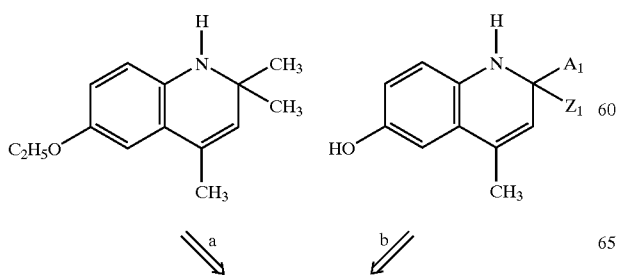

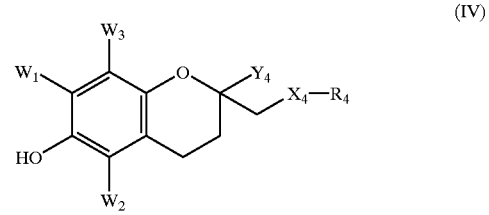

(III)

In addition, it should be recognized that some of the compounds of structure (III), including starting materials therefor, are commercially available from a number of sources. Further, various references disclose additional techniques, such as published Japanese Application No. JP 63/058455 A2 to Tamaki et al. and German Patent No. DE 2156371 (both of which are incorporated herein by reference), for the synthesis of compounds of structure (III).

In another aspect, the mitochondria protecting agents of this invention have the following structure (IV):

(IV)

including steroisomers and pharmaceutically acceptable salts thereof, wherein $W_1$, $W_2$ and $W_3$ are independently selected from —H and $C_{1-3}$alkyl;

$X_4$ is optionally selected from —NH—, —O— and —S—;

$Y_4$ is selected from —H and $C_{1-12}$alkyl; and $R_4$ is selected from —H, a guanidino moiety, a cylcoguanidino moiety, and a non-steroidal anti-inflammatory drug, or $X_4$—$R_4$ taken together is selected from —$CH_2OH$, —OC(=O)$CH_3$, and $C_{1-3}$ alkyl.

In one embodiment of structure (IV), $R_4$ is a guanidino moiety, and the compounds of this invention have the following structure (IV-1):

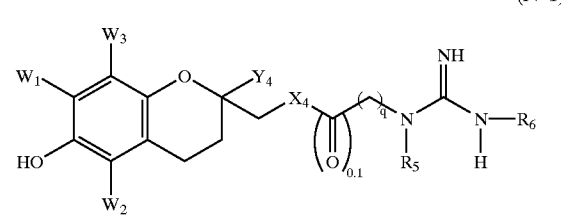

(IV-1)

In another embodiment of structure (IV), $R_4$ is cycloguanidino moiety, and the compounds of this invention have the following structure (IV-2):

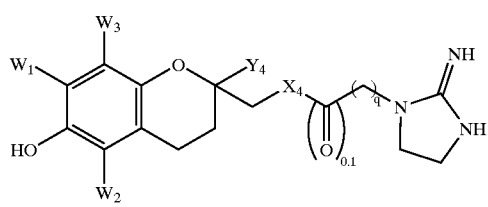

(IV-2)

In another embodiment of structure (IV), $X_4$ is O and $R_4$ is H as represented by structure (IV-3), or $X_4$ and $R_4$ taken together is a $C_{1-3}$alkyl as represented by structure (IV-4):

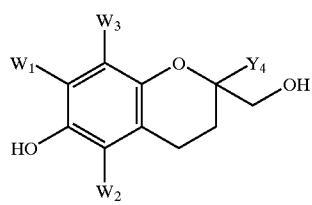

(IV-3)

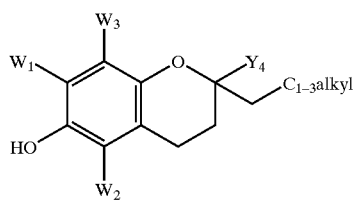

(IV-4)

In still a further embodiment of structure (IV), $R_4$ is a non-steroidal anti-inflammatory drug (NSAID). Such NSAIDs may be coupled via $X_4$ by formation of a suitable bond, such as an amide, ester or thioester linkage. Thus, when $X_4$ is oxygen, a an amide or ester may be formed to join the NSAID. For example, an ester linkage may be formed to join a compound of structure (IV) to naproxen, aspirin and ibuprofen as represented by the following structures (IV-6), (IV-7) and (IV-8):

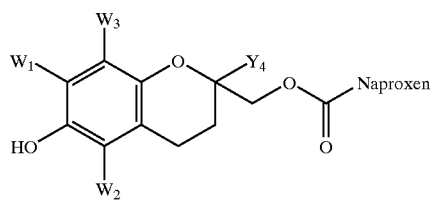

(IV-6)

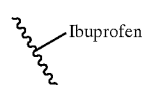

(IV-7)

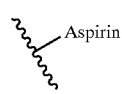

(IV-8)

Representative compounds of structure (IV) are set forth in the following Table 4.

TABLE 4

Representative Compounds

| Compound | $W_1, W_2, W_3$ | $Y_4$ | —$X_4$—$R_4$ | MW |
|---|---|---|---|---|
| (IV-3) | —$CH_3$ | —$CH_3$ | —OH | 236 |
| (IV-5) | —$CH_3$ | —$CH_3$ | —$CH_3$ | 220 |
| (IV-6) | —$CH_3$ | —$CH_3$ | —O—Naproxen | 434 |
| (IV-7) | —$CH_3$ | —$CH_3$ | —O—Aspirin | 398 |
| (IV-8) | —$CH_3$ | —$CH_3$ | —O—Ibuprofen | 424 |
| (IV-9) | —$CH_3$ | —$CH_3$ | —NHNHC(=NH)$NH_2$ | 292 |
| (IV-10) | —$CH_3$ | —$CH_3$ | —$OCOCH_3$ | 278 |

| Compound | $^1$H NMR δ (500 MHz, $CDCl_3$) |
|---|---|
| (IV-3) | 3.61 (m, 2H), 2.67 (m, 2H), 2.17 (s, 3H), 2.12 (s, 3H), 2.11 (s, 3H), 2.00 (m, 1H), 1.73 (m, 1H), 1.21 (s, 3H) |
| (IV-6) | 7.65 (m, 3H), 7.39 (m, 1H), 7.11 (m, 3H), 3.97–4.22 (m, 3H), 3.91 (s, 3H), 3.89 (m, 1H), 2.54 (br t, 1H), 2.46 (m, 1H), 2.12 (d, 3H), 1.57 (s, 3H) |
| (IV-7) | 7.84 (dd, 1H), 7.47 (t, 1H), 6.98 (d, 1H), 6.89 (t, 1H)4.36 (m, 2H), 2.68 (t, 2H), 2.33 (s, 3H), 2.34 (s, 3H), 2.09 (s, 3H), 2.02 (s, 3H), 1.39 (br s, 3H) |
| (IV-8) | 7.17 (dd, 2H), 7.06 (d, 1H), 7.01 (d, 1H), 4.07 (1H), 3.72 (q, 1H) 2.54 (t, 1H), 2.42 (m, 2H) 0.87 (m, 6H) |
| (IV-9) | 2.97 (s, 2H), 2.65 (t, 2H), 2.12 (s, 3H), 2.09 (s, 3H), 2.06 (s, 3H), 2.06–1.98 (m, 1H), 1.82–1.74 (m, 1H), 1.27 (s, 3H) (in $CD_3OD$) |
| (IV-10) | 4.25 (s, 1H), 4.11 (dd, 2H), 2.64 (t, 2H), 2.16 (s, 3H), 2.11 (s, 3H), 2.09 (s, 6H), 1.96–1.91 (m, 1H), 1.82–1.75 (m, 1H) 1.28 (s, 3H) |

The compounds of structure (IV) may be made by know organic reaction techniques, including those set forth in Example 9 below. For example, representative compounds of structure (IV) may be made from 6-hydroxy-2,5,7,8-tetramethylchroman-2-carboxylic acid (Trolox) as depicted below by reaction "a". Reduction of the acid group to the alcohol followed by optionally by coupling with a variety of different moieties, such as an NSAID, provides the corresponding compounds of structure (IV). For example, an aminoguanidine derivative may be prepared by reductive amination of the aldehyde using aminoguanidine and sodium cyanoborohydride. The aldehyde can be formed by Swem oxidation of the primary alcohol as described in the synthesis of Example 9 (see synthetic procedure of compound (IV-9)). The chroman system containing a methylamine substituent may be prepared by hydride reduction of the amide of Trolox via reaction "b". Keeping the phenolic hydroxyl protected, the amine may be coupled to a variety of moieties, such as NSAIDs, via reaction "c". Deprotection of the hydroxyl group then provides compounds of structure (IV) wherein —$X_4$—$R_4$ is, for example, —NH—NSAID.

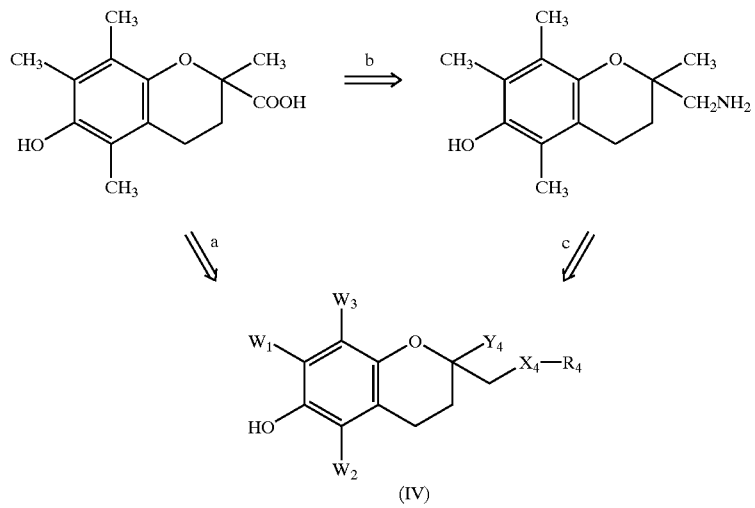

(IV)

In addition, it should be recognized that the starting materials for the synthesis of compounds of structure (IV) are commercially available from a number of sources.

Pharmaceutically acceptable salts of the compounds of this invention may be made by techniques well known in the art, such as by reacting the free acid or base forms of these compounds with a stoichiometric amount of the appropriate base or acid in water of in an organic solvent. Suitable salts in this context may be found in Remington's Pharmaceuitcal Sciences, 17$^{th}$ ed., Mack Publishing Co., Easton, Pa., 1985, which is hereby incorporated by reference.

A mitochondria protecting agent of this invention, or a pharmaceutically acceptable salt thereof, is administered to a patient in a therapeutically effective amount. A therapeutically effective amount is an amount calculated to achieve the desired effect. It will be apparent to one skilled in the art that the route of administration may vary with the particular treatment. Routes of administration may be either non-invasive or invasive. Non-invasive routes of administration include oral, buccal/sublingual, rectal, nasal, topical (including transdermal and ophthalmic), vaginal, intravesical, and pulmonary. Invasive routes of administration include intarterial, intravenous, intradermal, intramuscular, subcutaneous, intraperitoneal, intrathecal and intraocular.

The required dosage may vary with the particular treatment and route of administration. In general, dosages for mitochondria protecting agents will be from about 1 to about 5 milligrams of the compound per kilogram of the body weight of the host animal per day; frequently it will be between about 100 $\mu$g and about 5 mg but may vary up to about 50 mg of compound per kg of body weight per day. Therapeutic administration is generally performed under the guidance of a physician, and pharmaceutical compositions contain the mitochondria protecting agent in a pharmaceutically acceptable carrier. These carriers are well known in the art and typically contain non-toxic salts and buffers. Such carriers may comprise buffers like physiologically-buffered saline. phosphate-buffered saline, carbohydrates such as glucose, mannose, sucrose, mannitol or dextrans, amino acids such as glycine, antioxidants, chelating agents such as EDTA or glutathione, adjuvants and preservatives. Acceptable nontoxic salts include acid addition salts or metal complexes, eg., with zinc, iron, calcium, barium, magnesium, aluminum or the like (which are considered as addition salts for purposes of this application). Illustrative of such acid addition salts are hydrochloride, hydrobromide, sulphate, phosphate, tannate. oxalate, famarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

Mitochondria protecting agents of this invention also include prodrugs thereof. As used herein, a "prodrug" is any covalently bonded carrier that releases in vivo the active parent drug according the structures (I) through (IV) when such prodrug is administered to the animal. Prodrugs of the compounds of structures (I) through (IV) are prepared by modifying functional groups present on the compound in such a way that the modifications are cleaved, either in routine manipulation or in vivo, to the parent compound. Prodrugs include, but are not limited to, compounds of structures (I) through (IV) wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups.

The effectiveness of a compound of this invention as a mitochondria protecting agent may be determined by various assay methods. Suitable mitochondria protecting agents are active in one or more of the following assays for maintenance of mitochondrial structural and functional integrity, or in any other assay known in the art that measures the maintenance of mitochondrial structural and functional integrity. Accordingly, it is an aspect of the invention to provide methods for treating mitochondria associated diseases that include methods of administering compounds that may or may not have known antioxidant properties. However, according to this aspect of the invention, the unexpected finding is disclosed herein that mitochondria protecting agents may exhibit mitochondria protecting activities that are not predictable based upon determination of antioxidant properties in non-mitochondrial assay systems.

A. Assay for Inhibition of Production of Reactive Oxygen Species (ROS) Using Dichlorofluorescin Diacetate According to this assay, the ability of a mitochondria protecting agent of the invention to inhibit production of ROS intracellularly may be compared to its antioxidant activity in a cell-free environment. Production of ROS may be monitored using, for example by way of illustration and not limitation, 2',7'-dichlorodihydrofluorescein diacetate ("dichlorofluorescin diacetate" or DCFC), a sensitive indicator of the presence of oxidizing species. Non-fluorescent DCFC is converted upon oxidation to a fluorophore that can be quantified fluorimetrically. Cell membranes are also permeable to DCFC, but the charged acetate groups of DCFC are removed by intracellular esterase activity, rendering the indicator less able to diffuse back out of the cell.

In the cell-based aspect of the DCFC assay for inhibition of production of ROS, cultured cells may be pre-loaded with a suitable amount of DCFC and then contacted with a mitochondria protecting agent. After an appropriate interval, free radical production in the cultured cells may be induced by contacting them with iron (III)/ascorbate and the relative mean DCFC fluorescence can be monitored as a function of time.

In the cell-free aspect of the DCFC assay for inhibition of production of ROS, a mitochondria protecting agent may be tested for its ability to directly inhibit iron/ascorbate induced oxidation of DCFC when the protecting agent, the fluorescent indicator and the free radical former are all present in solution in the absence of cells.

Comparison of the properties of a mitochondria protecting agent in the cell-based and the cell-free aspects of the DCFC assay may permit determination of whether inhibition of ROS production by a mitochondria protecting agent proceeds stoichiometrically or catalytically. Without wishing to be bound by theory, mitochondria protecting agents that scavenge free radicals stoichiometrically (e.g., on a one-to-one molecular basis) may not represent preferred agents because high intracellular concentrations of such agents might be required for them to be effective in vivo. On the other hand, mitochondria protecting agents that act catalytically may moderate production of oxygen radicals at their source, or may block ROS production without the agents themselves being altered, or may alter the reactivity of ROS by an unknown mechanism. Such mitochondria protecting agents may "recycle" sothat they can inhibit ROS at substoichiometric concentrations. Determination of this type of catalytic inhibition of ROS production by a mitochondria protecting agent in cells may indicate interaction of the agent with one or more cellular components that synergize with the agent to reduce or prevent ROS generation. A mitochondria protecting agent having such catalytic inhibitor; characteristics may be a preferred agent for use according to the method of the invention.

Mitochondria protecting agents that are useful according to the instant invention may inhibit ROS production as quantified by this fluorescence assay or by other assays based on similar principles. A person having ordinary skill in the art is familiar with variations and modifications that may be made to the assay as described here without departing from the essence of this method for determining the effectiveness of a mitochondria protecting agent, and such variations and modifications are within the scope of this disclosure.

B. Assay for Mitochondrial Permeability Transition (MPT) Using 2-,4-Dimethylaminostyryl-N-Methylpyridinium (DASPMI)

According to this assay, one may determine the ability of a mitochondria protecting agent of the invention to inhibit the loss of mitochondrial membrane potential that accompanies mitochondrial dysfunction. As noted above, maintenance of a mitochondrial membrane potential may be compromised as a consequence of mitochondrial dysfunction. This loss of membrane potential or mitochondrial permeability transition (MPT) can be quantitatively measured using the mitochondria-selective fluorescent probe 2-,4-dimethylarninostyryl-N-methylpyridinium (DASPMI).

Upon introduction into cell cultures, DASPMI accumulates in mitochondria in a manner that is dependent on, and proportional to, mitochondrial membrane potential. If mitochondrial function is disrupted in such a manner as to compromise membrane potential, the fluorescent indicator compound leaks out of the membrane bounded organelle with a concomitant loss of detectable fluorescence. Fluorimetric measurement of the rate of decay of mitochondria associated DASPMI fluorescence provides a quantitative measure of loss of membrane potential, or MPT. Because mitochondrial dysfunction may be the result of reactive free radicals such as ROS, mitochondria protecting agents that retard the rate of loss of DASPMI fluorescence may be effective agents for treating mitochondria associated diseases according to the methods of the instant invention.

C. Assay of Apoptosis in Cells Treated with Mitochondria Protecting Agents

As noted above, mitochondrial dysfunction may be an induction signal for cellular apoptosis. According to this assay, one may determine the ability of a mitochondria protecting agent of the invention to inhibit or delay the onset of apoptosis. Mitochondrial dysfunction may be present in cells known or suspected of being derived from a subject with a mitochondria associated disease, or mitochondrial dysfunction may be induced in normal cells by one or more of a variety of physiological and biochemical stimuli with which those having skill in the art will be familiar.

In one aspect of the apoptosis assay, translocation of cell membrane phosphatidylserine (PS) from the inner to the outer leaflet of the plasma membrane is quantified by measuring outer leaflet binding by the PS-specific protein annexin. (Martin et al, $J.$ $Exp.$ $Med.$ 182:1545, 1995; Fakok et al., $J.$ $Immunol.$ 148:2207, 1992.) In another aspect of the apoptosis assay, induction of specific protease activity in a family of apoptosis-activated proteases known as the caspases is measured, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that may be known in the art (See, e.g, Ellerby et al., $J.$ $Neurosci.$ 17:6165–6178, 1997.) In another aspect of the apoptosis assay, quantification of the mitochondrial protein cytochrome c that has leaked out of mitochondria in apoptotic cells may provide an apoptosis indicator that can be readily determined. (Liu et al., $Cell$ 86:147, 1996) Such quantification of cytochrome c may be performed spectrophotometrically, immunochemically or by other well established methods for detecting the presence of a specific protein. A person of ordinary skill in the art will readily appreciate that there may be other suitable techniques for quantifying apoptosis, and such techniques for purposes of determining the effects of mitochondria protecting agents on the induction and kinetics of apoptosis are within the scope of the assays disclosed here.

D. Assay of Electron Transport Chain (ETC) Activity in Isolated Mitochondria As described above, mitochondria associated diseases may be characterized by impaired mitochondrial respiratory activity that may be the direct or indirect consequence of elevated levels of reactive free radicals such as ROS. Accordingly, a mitochondria protecting agent for use in the methods provided by the instant invention may restore or prevent further deterioration of ETC activity in mitochondria of individuals having mitochondria associated diseases. Assay methods for monitoring the enzymatic activities of mitochondrial ETC Complexes I, II, III, IV, and ATP synthetase, and for monitoring oxygen consumption by mitochondria, are well known in the art. (See, e.g., Parker et al., Neurology 44:1090–96, 1994; Miller et al, *J. Neurochem.* 67:1897, 1996.) It is within the scope of the methods provided by the instant invention to identify a mitochondria protecting agent using such assays of mitochondrial function. Further, mitochondrial function may be monitored by measuring the oxidation state of mitochondrial cytochrome c at 540 nm. As described above, oxidative damage that may arise in mitochondria associated diseases may include damage to mitochondrial components such that cytochrome c oxidation state, by itself or in concert with other parameters of mitochondrial function including but not limited to mitochondrial oxygen consumption, may be an indicator of reactive free radical damage to mitochondrial components. Accordingly, the invention provides various assays designed to test the inhibition of such oxidative damage by mitochondria protecting agents. The various forms such assays may take will be appreciated by those familiar with the art and is not intended to be limited by the disclosures herein, including in the Examples.

For example by way of illustration and not limitation, Complex IV activity may be determined using commercially available cytochrome c that is fully reduced via exposure to excess ascorbate. Cytochrome c oxidation may then be monitored spectrophotometrically at 540 nm using a stirred cuvette in which the ambient oxygen above the buffer is replaced with argon. Oxygen reduction in the cuvette may be concurrently monitored using a micro oxygen electrode with which those skilled in the art will be familiar, where such an electrode may be inserted into the cuvette in a manner that preserves the argon atmosphere of the sample, for example through a sealed rubber stopper. The reaction may be initiated by addition of a cell homogenate or, preferably a preparation of isolated mitochondria, via injection through the rubber stopper. This assay, or others based on similar principles, may permit correlation of mitochondrial respiratory activity with structural features of one or more mitochondrial components. In the assay described here, for example, a defect in Complex IV activity may be correlated with an enzyme recognition site.

The following examples are offered by way of illustration, and not by way of limitation.

EXAMPLES

Example 1

DCFC Assay for Inhibition of ROS Production by Mitochondria Protecting Agents

In the cell-based aspect of the DCFC assay, monolayers of cultured adherent SH-SY5Y human neuroblastoma cells (Biedler et al., *Cancer Res.* 33:2643, 1973) at or near confluence were rinsed and harvested using trypsin according to standard methods. Single cell suspensions containing $7.5\times10^4$ cells in 200 µl of medium were seeded into 96-well plates for overnight incubation at 37° C. and 5% $CO_2$ in a humidified cell atmosphere. The following day the wells were gently rinsed once with warm Hanks balanced saline solution (HBSS, Gibco-BRL), 200 µl of 30 µM dichlorofluorescin-diacetate (DCFC-DA, Molecular Probes, Eugene, Oreg.) were added to each well and cultures were incubated for 2 hours at 37° C./ 5% $CO_2$. The excess DCFC-DA was removed by needle aspiration and each well was gently rinsed twice with HBSS. Each well then received 80 µl of HBSS and 10 µl of mitochondria protecting agent, or vehicle control, diluted into HBSS from stock solutions of dimethylformamide or dimethylsulfoxide. The final concentration of the organic solvent was maintained at or below 0.1% (v/v) in HBSS while in contact with cells.

Cells were equilibrated for 15 minutes at room temperature with the mitochondria protecting agent (or vehicle control) and then 10 µl of fresh 500 µM ferric chloride/300 µM ascorbate solution was added to initiate free radical formation. Fluorescence of each microculture in the 96-well plate was quantified immediately using a Cytofluor fluorimetric plate reader (model #2350, Millipore Corp., Bedford, Mass.; excitation wavelength=485 nm, emission wavelength=530 µnm) and $t_0$ fluorescence was recorded. The 96-well plates were incubated 30 minutes at 37° C./5% $CO_2$ and fluorescence at 530 nm was again measured ($t_{30}$). The change in relative mean fluorescence (RMF) over the 30 minute period was calculated for each well.

The cells were then harvested by trypsinization and counted using a hemacytometer in order to normalize the data as $\Delta(t_{30},-t_0)$RMF per cell. The efficacy of a candidate mitochondria protecting agent was determined by comparing its ability to inhibit ROS production relative to the vehicle control.

In the cell-free aspect of the DCFC assay, candidate mitochondria protecting agents are further evaluated for their ability to inhibit ROS oxidation of DCFC in solution in a microtitre plate format. Stock compound solutions are usually prepared in dimethylformamide (DMF) or dimethylsulfoxide (DMSO) and diluted further into working concentrations using HBSS. Inhibition studies are carried out over a range of concentrations. Ten µl of the compound solution or vehicle control and 10 µl of a 300 µM DCFC solution in HBSS buffer are added to 60 µl of HBSS buffer. Ten pi of fresh 500 µM ferric chloride/ 300 µM ascorbate solution is then added to initiate free radical formation. Fluorescence of each well in the 96-well plate is quantified immediately using a Cytofluor tluorimetric plate reader (model #2350, Millipore Corp., Bedford, Mass.; excitation wavelength=485 nm; emission wavelength=530 nm) and fluorescence is recorded. Ten µl of a 0.5% aqueous $H_2O_2$ solution is then added to initiate hydroxyl radical formation through Fenton chemistry and a second fluorimetric reading is taken after 10 min. The concentration at which a candidate mitochondria protecting agent exerts 50% of its maximal inhibitory activity ($IC_{50}$) is calculated from a two-dimensional plot of relative fluorescence units against inhibitor concentration.

Data providing $IC_{50}$ values of representative mitochondria protecting agents of this invention in the cell-based assay described above are presented below in Table 6.

TABLE 6

Inhibition of ROS by Mitochondria Protecting Agents:
DCFC Assays

| Compound | $IC_{50}$ Cell-Based |
|---|---|
| (I-2) | 25 nM |
| (I-3) | 65 nM |
| (I-5) | 100 nM |
| (I-6) | 200 nM |
| (I-8) | 400 nM |
| (I-10) | 120 nM |
| (I-11) | 600 nM |
| (I-12) | 600 nM |
| (I-13) | 200 nM |
| (II-2) | 35 nM |
| (II-4) | 55 nM |
| (II-5) | 1 μM |
| (II-6) | 10 nM |
| (II-10) | 1 μM |
| (III-3) | 70 nM |
| (III-4) | 20 nM |
| (III-5) | 30 nM |
| (III-6) | 20 nM |
| (III-7) | 100 nM |
| (III-8) | 500 nM |
| (III-9) | 160 nM |
| (IV-3) | 300 nM |
| (IV-5) | 20 nM |
| (IV-6) | 30 nM |
| (IV-7) | 50 nM |
| (IV-8) | 40 nM |
| (IV-9) | 1 μM |

Example 2

Assay for Mitochondria Permeability Transition Using DASPMI

The fluorescent mitochondria-selective dye 2-,4-dimethylaminostyryl-N-methylpyridinium (DASPMI, Molecular Probes, Inc., Eugene, Oreg.) is dissolved in HBSS at 1 mM and diluted to 25 μM in warm HBSS. In 96-well microculture plates, cultured human cells from an individual known or suspected of having a mitochondria associated disease, or normal (control) cells, are incubated for 0.5–1.5 hrs in 25 μM DASPMI in a humidified 37 C/5% $CO_2$ incubator to permit mitochondrial uptake of the fluorescent dye. Culture supernatants are then removed and candidate mitochondria protecting agents diluted into HBSS from DNF or DMSO stocks, or vehicle controls, are added at various concentrations.

Fluorescence of each microculture in the 96-well plate is quantified immediately using a Cytofluor fluorimetric plate reader (model #2350, Millipore Corp., Bedford, Mass.; excitation wavelength=485 nm; emission wavelength=530 nm) and $t_0$ fluorescence is recorded. Thereafter, fluorescence decay is monitored as a function of time and the maximum negative slope (V-max) is calculated from a subset of the data using analysis software. In addition, the initial and final signal intensities are determined and the effects of candidate mitochondria protecting agents on the rate of signal decay is quantified.

Example 3

Effect of Mitochondria Protecting Agents on Apoptosis

In 96-well microculture plates. cultured human cells from an individual known or suspected of having a mitochondria associated disease, or normal (control) cells or cell lines, are cultured for a suitable period in the presence or absence of physiological inducers of apoptosis (e.g., Fas ligand. TNF-α, or other inducers of apoptosis known in the art) and in the presence or absence of candidate mitochondria protecting agents.

Exteriorization of plasma membrane phosphatidyl serine (PS) is assessed by adding to the 96 well plate annexin-fluorescein isothiocyanate conjugate (annexin-FITC, Oncogene Research Products, Cambridge, Mass.) dissolved in a suitable buffer for binding to cell surfaces at a final concentration of 5 μg/well. (Martin et al., *J. Exp. Med.* 182:1545, 1995) After 15–30 min in a humidified 37 ° C./ 5% $CO_2$ incubator, cells are fixed in situ using 2% formalin, washed to remove non-specifically bound FITC and read using a Cytofluor fluorimetric plate reader (model #2350, Millipore Corp., Bedford, Mass.; excitation wavelength=485 nm; emission wavelength=530 nm) to quantify cell surface bound annexin-FITC as a measure of outer leaflet PS, a marker for cells undergoing apoptosis.

Caspase-3 activity is assessed by diluting the fluorogenic peptide substrate Asp-Glu-Val-Asp-AMC (DEVD-AMC) from a DMSO stock solution into culture media to a final concentration of 20 μM for uptake by cells. Substrate cleavage liberates the fluorophore, which is measured continuously using a Cytofluor fluorimetric plate reader (model #2350, Millipore Corp., Bedford, Mass.; excitation wavelength=4355 nm; emission wavelength 460 nm). Caspase-1 is measured using the same protocol as that for caspase-3, except the caspase-1 specific fluorogenic substrate Tyr-Val-Ala-Asp-Z (Z-YVAD), is substituted for DEVD-AMC and fluorimetry is conducted using 405 nm excitation and 510 nm emission.

Cytochrome c released from mitochondria of cells undergoing apoptosis is recovered from the post-mitochondrial supernatant and quantified by reverse phase HPLC using a C-18 column, gradient elution (0–45% methanol in phosphate buffer, pH 7.4) and UV absorbance at 254 nm. Commercially-obtained authentic cytochrome c serves as the standard. Recovered cytochrome c is also quantified immunochemically by immunoblot analysis of electrophoretically separated post-mitochondrial supernatant proteins from apoptotic cells, using cytochrome c-specific antibodies according to standard and well accepted methodologies.

Example 4

Effect of Mitochondria Protecting Agents on Ionomycin Induced Apoptosis

SH-SY5Y neuroblastoma cells ($1 \times 10^5$ cells) are rinsed with one volume 1×PBS, and then treated with 10 μM ionomycin (Calbiochem, San Diego, Calif.) in DMEM supplemented with 10% fetal calf serum (FCS) (Gibco, Life Technologies, Grand Island, N.Y.) for 10 minutes, followed by two washes with DMEM (10% FCS). After 6h incubation at 37° C. in DMEM (10% FCS), cells are visualized by light microscopy (20X magnification). Approximately 80% of ionomycin treated cells exhibit membrane blebbing, indicative of entry by those cells into a final stage of apoptosis, compared to negligible apoptosis (<5%) in untreated cells. When cells are simultaneously treated with ionomycin and 2 mM creatine, the proportion of cells undergoing apoptosis as evidenced by membrane blebbing is reduced to approximately 10%. Candidate mitochondria protecting agents are assayed to determine whether they provides the same magnitude of protection from induction of apoptosis as does creatine in this ionomycin induced apoptosis assay.

Example 5

Effect of Mitochondria Protecting Agents on Ionomycin Induced Apoptosis

Control cybrid cells (MixCon) produced by fusing $\rho^0$ SH-SY5Y neuroblastoma cells with mitochondria source platelets from normal subjects, and 1685 cells, a cybrid cell line produced by fusing $\rho^0$ SH-SY5Y cells with mitochondria source platelets from an Alzheimer's Disease patient (Miller et al., 1996 J. Neurochem. 67:1897–1907), are grown to complete confluency in 6-well plates ($\sim 3 \times 10^6$ cells/well). Cells are first rinsed with one volume 1×PBS, and then treated with 10 µM ionomycin in the absence or presence of 100 µM of a candidate mitochondria protecting agent, in DMEM supplemented with 10% FCS, for 1 minute. At one minute, cells are rinsed twice with five volumes of cold 1×PBS containing a cocktail of protease inhibitors (2 µg/ml pepstatin, leupeptin, aprotinin, and 0.1 mM PMSF). Cells are then collected in one ml of cold cytosolic extraction buffer (210 mM mannitol, 70 mM mannitol, 5 mM each of HEPES, EGTA, glutamate and malate, 1 mM MgCl$_2$, and the protease inhibitor cocktail at the concentrations given above. Homogenization is carried out using a type B dounce homogenizer, 25× on ice. Cells are spun at high speed in an Eppendorf microfuge for five minutes to separate cytosol from intact cells, as well as cell membranes and organelles. The supernatant is collected and an aliquot saved, along with the pellet, at −80° C. for citrate synthase and protein assays.

Cytochrome c antibody is covalently bound to solid support chips containing a pre-activated surface (ProteinChip, Ciphergen, Palo Alto, Calif.). The spot to be treated with antibody is initially hydrated with 1 µl of 50% CH$_3$CN and the antibody solution is added before the CH$_3$CN evaporated. The concentration of the antibody is approximately 1 mg/ml in either Na$_3$PO$_4$ or PBS buffer (pH 8.0). The chip is placed in a humid chamber and stored at 4° C. overnight. Prior to addition of the cytosolic extract, residual active sites are blocked by treatment with 1.5 yl ethanolamine (pH 8.0) for thirty minutes. The ethanolamine solution is removed and the entire chip is washed in a 15 ml conical tube with 10 ml 0.05% Triton-X 100 in 1×PBS. for 5 minutes with gentle shaking at room temperature. The wash buffer is removed and the chip is sequentially washed. first with 10 ml 0.5 M NaCl in 0.1 M NaOAc (pH 4.5), and then with 0.5 M NaCl in 0.1 M Tris (pH 8.0). After removal of the Tris-saline buffer, the chip is rinsed with 1×PBS and is ready for capture of the antigen.

Fresh supernatant samples are spotted onto the Ciphergen ProteinChip containing covalently-linked anti-cytochrome c antibody (Pharmingen. San Diego, Calif.). For optimal antibody-cytochrome c interaction, 100 µl of the supernatant is used and the incubation is carried out overnight with shaking at 4° C. in a Ciphergen bioprocessing unit. The supernatant is then removed and the spots on the chip are washed in the bioprocessing unit three times with 200 µl of 0.1% Triton-X 100 in 1×PBS, and then twice with 200 µl of 3.0 M urea in 1×PBS. The chips are then removed from the bioprocessor and washed with approximately 10 ml of dH$_2$O. The chips are then dried at room temperature prior to the addition of EAM solution (e.g. sinapinic acid, Ciphergen, Palo Alto, Calif.). A suspension of the EAM is made at a concentration of 25 mg/ml in 50% CH$_3$CN/H$_2$O containing 0.5% TFA. The saturated EAM solution is clarified by centrifugation and the supernatant is used for spotting on the ProteinChip surface. Prior to the addition of EAM to the chip, an internal standard of ubiqutin is added to the EAM solution to provide a final concentration of 1 pmol/µl. The quantification of cytochrome c released from mitochondria upon ionomycin treatment is based on normalization to the ubiquitin peak in the mass spectrum and the protein content of the cytosolic extracts. Citrate synthase activity of cytosolic extracts is measured to rule out the possibility of mitochondrial lysis during the sample preparation procedure. Data from this assay may be represented, for example, by graphing cytochrome c release in cells undergoing ionomycin induced apoptosis, and attenuation of cytochrome release in cells treated with a candidate mitochondria protecting agent compound at the same time ionomycin is introduced.

Example 6

Synthesis and Characterization of Representative Mitochondria Protecting Agents of Structure (I)

This example illustrates the synthesis and characterization of representative mitochondria protecting agents having structure (I) of this invention.

Structure (I-6):

To a solution of 123 mg (0.75 mmole) of 4-allyl-2-methoxyphenol (eugenol) and 1.4 gm (7.5 mmole)of p-toluenesulfonhydrazide in 15 ml of dimethoxyethane under reflux was added a solution of 1.7 gm of NaOAc in 15 ml water over a 4 hour period. The mixture was cooled to room temperature, poured into 20 ml of water, and extracted three times with 30 ml of CH$_2$Cl$_2$. The combined organic layers were washed with 50 ml of water, dried over MgSO$_4$, and concentrated under vacuo. The resulting solid was flash chromatographed over silica gel using 10% ethyl acetate in hexane to afford 60 mg of 2-methoxy-4-propylphenol in 48% yield.

To 38 mg (0.23 mmole) of 2-methoxy4fpropylphenol in 0.4 ml of CH$_2$Cl$_2$ at −78° C. and under argon was added 254 µl (0.252 mmole) of a 1M BBr$_3$ solution in CH$_2$Cl$_2$. The reaction mixture was stirred at −78° C. for one hour and then warmed to 0° C. The reaction was quenched by addition of 2 ml of water. The mixture was extracted three times with 5 ml of CH$_2$Cl$_2$ dried over anhydrous Na$_2$SO$_4$ and concentrated by rotary evaporation. The crude product was flash chromatqgraphed over silica gel using 25% ethyl acetate in hexane to farnish 30 mg of 2-hydroxy4-propylphenol, Structure (I-6), in 86% yield.

Structure (I-8):

To 60 mg (0.39 mmole) of 2-hydroxy4-propylphenol under argon was added 0.9 ml of pyridine and 0.75 ml of acetic anhydride. The mixture was stirred for 18 hours at 23° C. The reaction mixture was then taken up in 35 ml hexane, washed with 10 ml of brine, dried over anhydrous Na$_2$SO$_4$ and concentrated. The product was purified by flash chromatography over silica gel using 15% ethyl acetate in hexane to provide 87 mg of Structure (I-8) in 93% yield.

Structure (I-2):

Concentrated sulfuric acid (204 µl) was carefully added of to 700 µl of water at 0° C. Then 223 mg (2.63 mmole) of NaiO$_3$ was added and the mixture was stirred at 0° C. till the salt went into solution. 4-Octylphenol (309 mg; 1.5 mmole) was then added in two equal portions. The reaction mixture turned reddish in color. The reaction was allowed to proceed at 0° C. for 10 min and then at 23° C. for 3 hours. The mixture was taken up in 60 ml of ethyl acetate, washed with 20 ml of brine, dried over anhydrous Na$_2$SO$_4$ and concentrated. Purification by flash chromatography using 5% ethyl acetate in hexane provide 257 mg of 2-nitro-4-octylphenol in 68% yield.

To 95.4 mg(0.38 mmole) of 2-nitro-4-octylphenol in 2 ml of 1:1 glacial acetic acid and water mixture at 85–90° C. was added 0.35 gm of activated iron in three portions over a 15 min period. The reaction was allowed to proceed at the same temperature for 45 min. The reaction mixture was diluted then with 5 ml of water and extracted pith 20 ml ethyl acetate. The organic layer was dried over anhydrous Na$_2$SO$_4$ and concentrated by rotary evaporation. The crude product was flash chromatographed over silica gel using 30% ethyl acetate in hexane to yield 56 mg of 2-amino4octyl phenol, Structure (I-2), in 67% yield.

Structure (I-3):

The compound of Structure (I-3) may be prepared in the same manner as set forth above for Structure (I-2), but using t-octylphenol in place of 4-octylphenol.

Example 7

Synthesis and Characterization of Representative Mitochondria Protecting Agents of Structure (II)

This example illustrates the synthesis and characterization of representative mitochondria protecting agents having structure (II) of this invention.

Structure (II-4):

Concentrated sulfuric acid (816 μl) was added dropwise to 2.8 ml water at 0° C., following which 892 mg (10.5 mmole) NaNO$_3$ was added and dissolved by magnetic stirring at 0° C. 4,4'-Isopropylidenediphenol (682 mg, 3 mmole) was added and the mixture was stirred for 15 minutes at 0° C. and then for 16 hours at 23° C. The reaction products were taken up in 120 ml of ethyl acetate, washed with 50 ml of water, dried over anhydrous Na$_2$SO$_4$ and concentrated. The crude material was flash chromatographed over silica gel using 10% ethyl acetate in hexane to afford 200 mg (24% yield) of the mono-nitro derivative and 457 mg (48% yield) of the di-nitro compound.

To 66 mg (0.24 mmole) of the mono-nitro compound in 2 ml of 1:1 glacial acetic acid and water at 85–90° C. was added 0.3 gm activated iron in 3 portions over a 15 minute period. The reaction was allowed to proceed at the same temp for 45 min, with stirring. The reaction mixture was then diluted with 5 ml of water, extracted with 20 ml of ethyl acetate, dried over anhydrous Na$_2$SO$_4$ and concentrated. Silica gel flash chromatography of the crude product using 10% methanol in chloroform provided 55.7 mg of Structure (II4) in 96% yield.

Structure (II-2):

Structure (II-2) was prepared by a similar procedure from the di-nitro compound in 45% yield.

Structure (II-6):

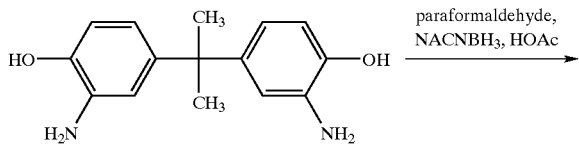

paraformaldehyde, NACNBH$_3$, HOAc

-continued

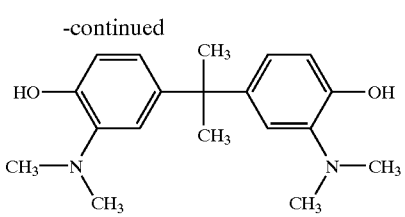

To 25 mg of the diamine in 0.85 ml of acetic acid was added 33 mg of paraformaldehyde and 71 mg of NaCNBH$_3$. The solution was stirred for 16 hrs at 23° C. and then poured into 20 ml of saturated NaaHCO$_3$ and then extracted with 2×25 ml of ethyl acetate. The solution was dried over anhydrous Na$_2$SO$_4$, concentrated and the residue was purified by flash chromatography using a 5% CH$_3$OH/CHCl$_3$ solvent system to afford 17 mg of the hexamethyl-benzhydryl derivative in 54% yield. (The N-methyl analogue of 2,2,4-trimethyl-1,2-dihydro-quinolin-6-ol, structure (III-11) may be prepared in an analogous manner.)

Structure (II-9)

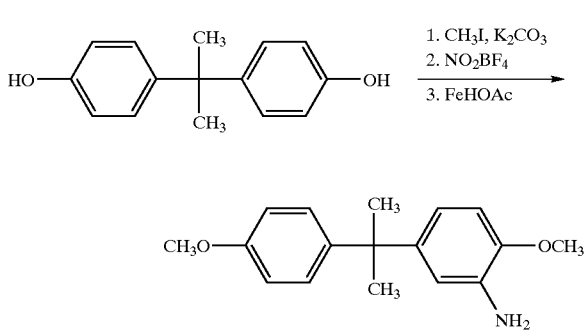

To 171 mg of 4,4-isopropylidenediphenol (0.75 mmole) in 5 ml of dry DME was added 1.12 gm of K$_2$CO$_3$ and 396 μl of CH$_3$I (6.4 mmol) and the mixture was refluxed for 16 hours. The mixture was filtered, the residue was washed with ethyl acetate and combined with the filtrate. The solution was evaporated and the crude compound was flash chromatographed using 30% ethyl acetate in hexane to afford the 118 mg of dimethoxy derivative as one of the products (69% yield).

To 77 mg of the dimethoxy derivative in 560 ml of dry sulfolane at 4° C. was added 590 ml of a 0.5 M solution of nitronium tetrafluoroborate in sulfolane. The mixture was stirred for 15 min under argon, then diluted with 80 ml of ethyl ether. The solution was washed with 4×20 ml of water, dried over anhydrous magnesium sulfate and concentrated. The products were subjected to silica gel flash chromatography using 30% ethyl acetate in hexane to afford 29 mg of mono-nitrated product and 15 mg of the di-nitro derivative.

To 36 mg of the mono-nitro derivative in 1 ml of 1:1 glacial acetic acid/H2O was added 130 mg of activated iron and the mixture was refluxed at 85–90° C. for 45 min. Water (5 ml) was then added and the product was extracted with ethyl acetate, and concentrated in vacuo. The product was then purified by preparative thin layer chromatography using 50% ethyl acetatefhexane as the eluting system.

Structure (II-10):

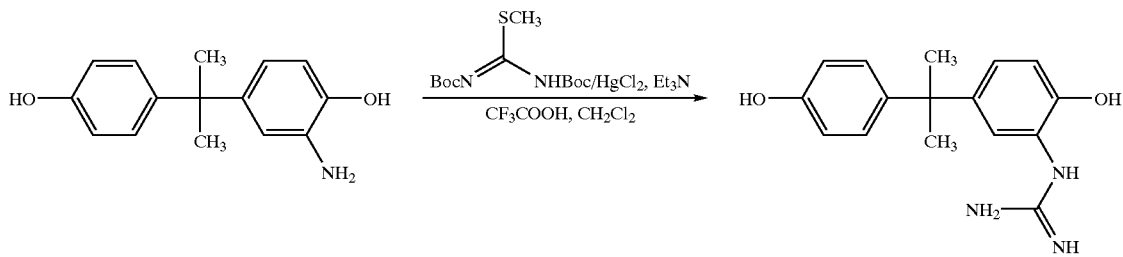

To a round-bottomed flask fitted with an argon inlet were placed compound (II-4) (30 mg, 0.123 mmol), 1,3-bis(tert-butoxycarbonyl)-2-methyl-2-thiopseudourea (II-46 mg, 0.16 mmol) and dry N,N-dimethylformamide (630 µl). To the above stirred solution at room temperature were added triethylamine (52 µl, 0.37 mmol) and mercuric chloride (37 mg, 0.13 mmol). The resulting mixture was stirred at room temperature, whereupon a white precipitate soon formed. After stirring for 3 h, the reaction mixture was diluted with ethyl acetate and filtered through a pad of Celite. The filtrate was washed with 5% aqueous sodium carbonate (1×10 ml), water (2×10 ml) and brine (1×10 ml). The solution was dried over anhydrous magnesium sulfate and concentrated to provide the crude product. Purification by flash chromatography using 20% ethyl acetatehexane provided 45 mg of the Bocprotected guanidine derivative.

Deprotection of the Boc group was achieved by treatment with trifluoroacetic acid (TFA). Thus, to 45 mg of the benzhydryl-Boc derivative under argon was added 1 ml of 50% TFA/CH$_2$Cl$_2$ solution and the mixture was stirred for 3 h at 23° C. The solvent was then removed by rotary evaporation to provide 27 mg of pure guanidine derivative of structure (II-10) (single spot by TLC using 20% CH$_3$OH/CHCl$_3$ solvent system containing 1% HOAc).

Example 8

Synthesis and Characterization of Representative Mitochondria Protecting Agents of Structure (III)

This example illustrates the synthesis and characterization of representative mitochondria protecting agents having structure (III) of this invention.

Coupling of NSAIDs with 6-ethoxy-1,2-dihydro-2,2,4-trimethylguinoline (ethoxyguin)

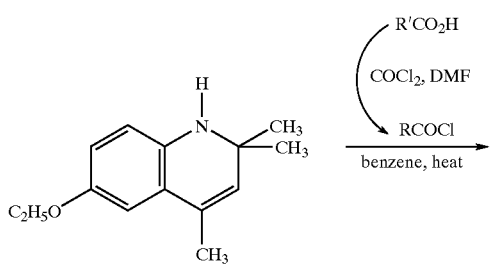

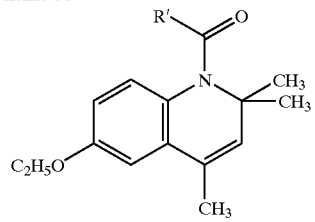

R'CO$_2$H = ibuprofen (IV-8)
acetyl salicylic acid (IV-7)
naproxen (IV-6)

Ibuprofen, (S)-(+)-4isobutyl-α-methylphenylacetic acid, and naproxen, (S)-(+)-6-methoxy-α-2-methyl-2-naphthaleneacetic acid, were converted to their acid chlorides by the procedure described below. Acetyl salicyloyl chloride is commercially available from Aldrich Chemical Co. (Milwaukee, Wis.). The ibuprofen conjugate preparation is representative of the coupling procedure. Thus, to 103 mg (0.5 mmol) of ibuprofen in 7 ml of dry benzene was added 54 µl of oxalyl chloride that results in rapid gas evolution. The mixture was stirred for 30 min at 23° C. and then the solvent was removed by rotary evaporation. The oily residue was taken up in 7 ml of dry THF and the solvent was evaporated again to remove traces of oxalyl chloride. The acid chloride product was kept under high vacuum for an additional 30 min and used in the next step without purification. A solution of 74 µl (~0.35 mmol) of ethoxyquin and the acid chloride from the previous reaction in 1 ml of dry benzene was stirred for 72 hrs at 23° C. followed by reflux for 4 hrs. The solvent was removed in vacuo and the product was purified by flash chromatography using 13% ethyl acetateihexane solvent system to furnish 82 mg of the ibuprofen conjugate in 57% yield. The naproxen conjugate and the acetylsalicylic acid conjugate were obtained in 57% and 10% yields respectively.

Synthesis of 6-alkylthio-1,2-dihydro-2,2,4-trimethylquinolines

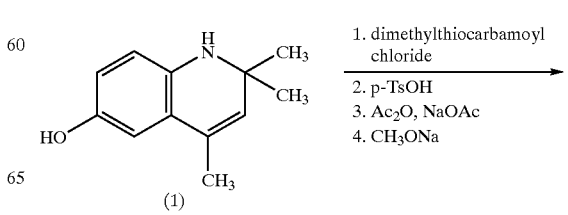

(1)

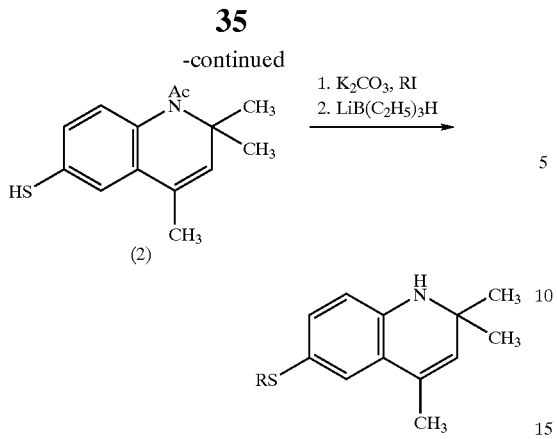

6-Alkylthio-1,2-dihydro-2,2,4-trimethylquinolines are prepared by a two step procedure from 1-acetyl-1,2-dihydro-2,2,4-trimethylquinoline-6-thiol (1). Compound (2) was synthesized by the procedure described by Pearce and Wright (U.S. Pat. No. 5,411,969) from 2,2,4trimethyl-1,2ihydroquinolin-6-ol (1), that is listed in the Salor catalogue (S13857–8) and can be ordered through Sigma or Aldrich Chemicals. Briefly, (2) is synthesized by treatment of (1) with dimethylthiocarbamoyl chloride to afford the O-aryl dimethyl thiocarbamate that is rearranged to the S-aryl thiocarbamate using p-toluenesulfonic acid as the acid catalyst. The resulting intermediate is reacted with acetic anhydride to provide the N-acetyl derivative that is then treated with sodium methoxide in methanol to unmask the dimethylthiocarbamate to furnish the thiol (2).

Synthesis of 1,2-dihydro-6-thiomethoxy-2,2,4-trimethylquinoline

To 150 mg (0.61 mmol) of 1-acetyl-1,2-dihydro-2,2,4-trimethylquinoline-6-thiol (2) in 3 ml of anhydrous acetonitrile and under argon was added 126 mg (0.92 mmol) of potassium carbonate and 38 μl (0.61 mmol) of methyl iodide. The mixture was stirred at room temperature for 2 hours and then was taken up in 30 ml of ethyl acetate. washed with water and then brine. The organic layer was dried over anhydrous $MgSO_4$, filtered and concentrated. 1-Acetyl-1,2,4-dihydro-6-thiomethoxy-2,2,4-trimethylquinoline was purified by silica gel flash chromatography using ethyl acetate/hexane as the eluting system.

To 1-acetyl-1,2-dihydro-2,2,4-methylquinoline-6-thiol (90 mg, 0.35 mmol) in 2 ml of dry THF at −10° C. and under argon was added in dropwise fashion 1.75 ml of a 1 M THF solution of lithium triethylborohydride. The mixture wasstirred for 10 min, then warmed to 23° C. and stirred for an additional 16 hours. Excess borohydride reagent was quenched by addition of saturated $NH_4Cl$. The mixture was poured into water and then extracted with ethyl acetate. The organic layer was then washed with brine, dried over anhydrous $MgSO_4$, filtered and concentrated. The crude aterial was purified by silica gel flash chromatography using ethyl acetate,lhexane to yield pure 1,2-dihydro-6-thiomethoxy-2,2,4-trimethylquinoline.

Example 9

Synthesis and Characterization of Representative Mitochondria Protecting Agents of Structure (IV)

6-t-butyldimethylsilyloxy-2,5,7,8-tetramethylchroman-2-carboxylic acid t-butyldimethylsilyl ester To 500 mg (2 mmole) of Trolox in 2.8 ml of anhydrous DMF and under argon was added 952 mg (14 mmole) of imidazole and 1.06 gm (7 mmole) of t-butyldimethylsilyl chloride and the mixture was stirred at 23° C. for 72 hours. The reaction mixture was taken up in 200 ml of $CH_2Cl_2$ and washed successively with 30 ml each of saturated sodium bicarbonate and brine. The organic layer was dried over anhydrous $Na_2SO_4$ and then the solvent was removed in vacuo to provide 2.01 gm of crude reaction product. The carboxylic acid derivative was used in the next step without further purification (6-t-butyldimethylsilyloxy-2,5,7,8-tetramethyl-3,4-dihydro-2H-1-benzo[1,2-b]pyran-2yl)methanol To 511 mg (13.8 mmole) of lithium aluminum hydride (LAH) under argon was added 17 ml of anhydrous THF and the mixture was cooled to 0° C. The crude reaction product (2.01 gm) from the previous reaction was dissolved in 24 ml of anhydrous THF and the solution was added dropwise to the LAH suspension. The reaction mixture was stirred at 0° C. for 2 hours following which excess LAH was quenched by addition of saturated aqueous sodium sulfate solution. The resulting flocculate was poured over a bed of celite in a sintered glass funnel and ~150 ml ethyl acetate was used to wash the celite bed. The solvent was removed by rotary evaporation and the desired silyl ether-alcohol derivative was purified by silica gel flash chromatography using chloroform to provide 583 mg (83% yield for two steps) of isolated material. $^1H$ NMR (500 MHz. $CDCl_3$) d 3.60 (m, 2H), 2.10 (m, 2H), 2.10 (s. 3H), 2.07 (s, 3H)2.06 (s, 3H), 1.21 (s. 31H). 1.05 (s. 9H), 0.119 (s, 3H)116 (s. 3H).

Structure (IV-6) (Chormanol-Nuuproxen Coniugate)

To 57.3 mg (0.16 mmole) of (6-t-butyldimethylsilyloxy-2,5,7,8-tetramethyl-3,4dihydro-2H-1-benzo[1,2-b]pyran-2yη)methanol in 1.7 ml of dry $CH_2Cl_2$ was added 37.5 mg (0.16 mmol) of (+)-6-methoxy-α-methyl-2-napthaleneacetic acid (naproxen), 37 mg (0.18 mmole) 1,3-dicyclohexylcarbodiimide and 5.7 mg of 4-dimethylamino pyridine. The reaction mixture was stirred under argon for five hours and then the urea byproduct was removed by filtration. The product of the coupling reaction was purified by flash chromatography over silica gel using 10% ethyl acetate in to afford 78.2 mg (85%G) of pure material.

To a solution of 30.7 mg (0.06 mmole) of the above silyloxy ether derivative in 1 ml of anhydrous THF at 0° C. and under argon was added 164 μl (0.164 mmole) of a 1 M tetrabutylarunoniumfluoride solution in THF. The reaction was kept at 0° C. for 10 min and then at 23° C. for 30 min. The mixture was taken up in 30 ml ethyl acetate, washed with brine, dried over anhydrous $Na_2SO_4$ and concentrated. The naproxen-chromanol conjugate was purified by preparatory thin layer chromatography using 20% ethyl acetate in hexane as the eluting solvent to provide 6 mg of purified material.

Structure (IV-7) (Chromanol-Salicylic acid Conjugate)

Structure (IV-7) was made in the same manner as disclosed above, but employing salicylic acid in place of naproxen.

Structure (IV-8) (Chromanol-Ibuprofen Conjugate)

Structure (IV-8) was made in the same manner as disclosed above, but employing salicylic acid in place of naproxen.

Structure (IV-3)

To a suspension of 251 mg (6.6 mmole) of LAH in 2 ml of anhydrous THF was added dropwise a solution of trolox (0.5 gm, 2 mmole) in 10 ml of anhydrous THF The solution was stirred for two hours and excess LAH was quenched by addition of saturated aqueous sodium sulfate solution. The aluminium salts were removed by filtering through a celite bed, the organic solution was dried over anhydrous NaSO₄ and concentrated. The crude mixture was purified by silica gel flash chromatography using 0.5/1/98.5 methanol/acetic acid/chloroform eluent to afford 323 mg (68%) of Structure (IV-3).

Structure (IV-9)

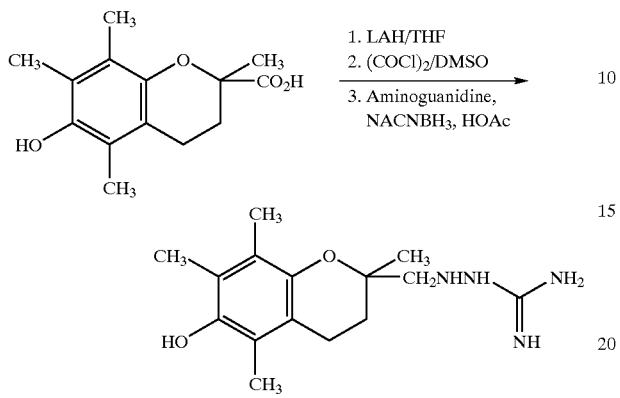

Lithium aluminium hydride (473 mg, 12.7 mmol) was suspended in 10 ml of dry THF and 1 gm of Trolox (4 mmol) in 12 ml of THF was added under argon. The reaction mixture was stirred for 2 hrs at 23° C. and then quenched by carefully pouring it into an ice/water mixture. The aqueous layer was extracted with 100 ml of ethyl acetate. The organic layer was separated, washed with brine, dried over anhydrous Na₂SO₄, and concentrated. The residue was purified by flash chromatography using 1:1:98 methanol/acetic acid/CHCl₃ solvent system to afford 936 mg of diol (94% yield).

The primary alcohol was oxidized to the aldehyde using Swem oxidation conditions. Thus, to oxalyl chloride (100 μl) in 2 ml of CH₂Cl₂ at −78° C. and under N₂ was added 100 μl of DMSO and the reaction mixture was stirred for 10 min. A solution of 97 mg of the above diol in 1 ml of CH₂Cl₂ was then added and the reaction was stirred for 15 min. Triethylamine (750 μl) was then added and the mixture was warmed to 23° C. Water (1.5 ml) was then added and the mixture was stirred for an additional 10 min. The crude product was extracted with CH₂Cl₂, dried over anhydrous Na₂SO₄ concentrated and flash chromatographed using 25% ethyl acetate in hexane to furnish 56 mg of the aldehyde in 67% yield. This material was used immediately in the subsequent reaction.

A mixture of 46 mg of aldehyde (0.2 mmol), 43.3 mg of aminoguanidine (0.4 mmol) and 123 mg of NaCNBH₃ in 2 ml of acetic acid was stirred for 16 hrs at 23° C. The reaction mixture was then poured into 50 ml of saturated NaHCO₃ and then extracted with 2×50 ml of ethyl acetate. The solution was dried over anhydrous Na₂SO₄, concentrated and the residue was purified by flash chromatography using a 1:14:85 HOAc/CH₃OH/CHCl₃ solvent system to afford 54 mg of structure (IV-9). MS 293.3 (M+1)

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating Alzheimer's Disease, Parkinson's Disease, diabetes mellitus, or stroke by administering to a warm-blooded animal in need thereof an effective amount of a compound having the following structure (III):

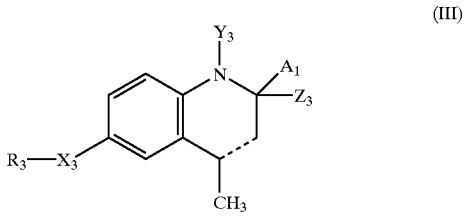

(III)

or a steroisomer, prodrug or pharmaceutically acceptable salt thereof, wherein the dotted line represents a single or double bond;

$A_1$ is selected from —H and $C_{1-3}$alkyl;

$Y_3$ is —COR$_d$;

$Z_3$ is selected from —H, $C_{1-3}$alkyl and —(CH$_2$)$_m$X$_3$R$_d$;

$X_3$ is selected at each occurrence from —S—, —O— and —NH—;

$R_3$ is selected from —H, —CH$_3$, —CH$_2$CH$_3$ and —R$_d$;

$R_d$ is selected from a guanidino moiety, a cylcoguanidino moiety, and a non-steroidal anti-inflammatory drug; and m is 1–4.

2. The method of claim 1 wherein $R_3$ is —H, —CH$_3$ or —CH$_2$CH$_3$.

3. The method of claim 1 wherein $X_3$ is —O—.

4. The method of claim 1 wherein $A_1$ is —CH$_3$.

5. The method of claim 1 wherein $Z_3$ is —CH$_3$.

6. The method of claim 1 wherein $Y_3$ is —H or —CH$_3$.

7. The method of claim 1 wherein $Y_3$ is —COR$_d$.

8. The method of claim 1 wherein $R_d$ is a non-steroidal anti-inflammatory drug (NSAID).

9. The method of claim 8 wherein the NSAID is ibuprofen, aspirin or naproxen.

* * * * *